United States Patent
Edlund et al.

(10) Patent No.: US 9,782,424 B2
(45) Date of Patent: Oct. 10, 2017

(54) SYNERGISTIC COMBINATION COMPRISING AVERMECTINS AND A NSAID FOR TUMOR INHIBITION

(71) Applicant: Ectin Research AB, Hovas (SE)

(72) Inventors: Christer Edlund, Hovas (SE); Peter Falk, Grabo (SE); Marie-Lois Ivarsson, Hovas (SE)

(73) Assignee: ECTIN RESEARCH AB, Hovas (SE)

( * ) Notice: Subject to any disclaimer, the term of this patent is extended or adjusted under 35 U.S.C. 154(b) by 0 days.

(21) Appl. No.: 14/366,604

(22) PCT Filed: Dec. 20, 2012

(86) PCT No.: PCT/SE2012/051456
§ 371 (c)(1),
(2) Date: Jun. 18, 2014

(87) PCT Pub. No.: WO2013/095286
PCT Pub. Date: Jun. 27, 2013

(65) Prior Publication Data
US 2014/0371164 A1 Dec. 18, 2014

(30) Foreign Application Priority Data
Dec. 20, 2011 (SE) .................................... 11512233

(51) Int. Cl.
| | | |
|---|---|---|
| *A61K 31/7048* | (2006.01) | |
| *A61K 31/192* | (2006.01) | |
| *A61K 31/196* | (2006.01) | |
| *A61K 31/415* | (2006.01) | |
| *A61K 31/4164* | (2006.01) | |
| *A61K 31/496* | (2006.01) | |
| *A61K 45/06* | (2006.01) | |
| *A61K 31/4184* | (2006.01) | |

(52) U.S. Cl.
CPC ........ *A61K 31/7048* (2013.01); *A61K 31/192* (2013.01); *A61K 31/196* (2013.01); *A61K 31/415* (2013.01); *A61K 31/4164* (2013.01); *A61K 31/4184* (2013.01); *A61K 31/496* (2013.01); *A61K 45/06* (2013.01)

(58) Field of Classification Search
CPC .............. A61K 31/7048; A61K 31/192; A61K 31/196; A61K 31/496; A61K 31/4184
See application file for complete search history.

(56) References Cited

U.S. PATENT DOCUMENTS 6,114,376 A * 9/2000 Prichard .............. A61K 31/365 514/450
6,693,125 B2 * 2/2004 Borisy ................. A61K 31/415 514/388

FOREIGN PATENT DOCUMENTS

| EP | 1 066 854 A2 | 1/2001 |
|---|---|---|
| EP | 1 428 528 A1 | 6/2004 |
| JP | 2005/247807 A | 9/2005 |
| WO | WO 03/080044 A1 | 10/2003 |
| WO | WO 2009/060063 A1 | 5/2009 |

OTHER PUBLICATIONS

Alvinerie M. et al. "Ketoconazole increases the plasma levels of ivermectin in sheep", *Veterinary Parasitology*, vol. 157(1-2), Oct. 20, 2008, pp. 117-122.
Anonymous, "Stromectol (R) (Ivermectin) Tablets", *Merck Prescribing Information*, 2007, pp. 1-7.
Bartley, D.J. et al. "Influence of Pluronic 85 and ketoconazole on disposition and efficacy of ivermectin in sheep infected with a multiple resistantisolate", *Veterinary Parasitology*, vol. 187(3), Feb. 19, 2012, pp. 464-472.
Drinyaev, V.A. et al. "Antitumor effect of avermectins", *European Journal of Pharmacology*, vol. 501(1-3, 6), Oct. 6, 2004, pp. 19-23.
International Preliminary Report on Patentability Corresponding to International Application No. PCT/SE2012/051456; datedJun. 24, 2014.
International Search Report and Written Opinion Corresponding to International Application No. PCT/SE2012/051456; datedSep. 17, 2013.
Johnson, D.E. et al. "Ketoconazole therapy for hormonally refractive metastatic prostate cancer", *Urology*, vol. 31(2), Feb. 1, 1988, pp. 132-134.
Jones, A.L. et al. "Treatment of advanced breast cancer with miconazole: a potential inhibitor of peripheral oestrogen synthesis", *European Journal of Cancer and Clinical Oncology*, vol. 27(3), Jan. 1, 1991, p. 301.
Lorusso, P. et al. "Effect of coadministration of ketoconazole, a strong CYP3A4 inhibitor, on pharmacokinetics and tolerability of motesanib diphosphate (AMG 706) in patients with advanced solid tumors", *Investigational New Drugs: The Journal of New Anticancer Agents*, vol. 26(5), Jun. 24, 2008, pp. 455-462.
Rothova, A. et al. "Side-effects of ivermectin in treatment of onchocerciasis", *The Lancet*, vol. 333(8652), Jun. 24, 1989, pp. 1439-1441.

* cited by examiner

*Primary Examiner* — Layla Berry
*Assistant Examiner* — Bahar Craigo
(74) *Attorney, Agent, or Firm* — Myers Bigel, P.A.

(57) ABSTRACT

The present invention includes a composition comprising an effective amount of an avermectin compound, and an effective amount of an imidazole antifungal compound, and/or an effective amount of non-steroidal anti-inflammatory drug (NSAID) or suitable pharmaceutically acceptable salts thereof, for use in the inhibition of tumor growth and treating urothelial, colorectal, prostate and/or breast cancers. Furthermore, the invention includes a method of inhibiting tumor growth and treating said cancers comprising administering to a subject in need thereof an effective amount of said composition.

23 Claims, 6 Drawing Sheets

SYNERGISTIC COMBINATION COMPRISING AVERMECTINS AND A NSAID FOR TUMOR INHIBITION

STATEMENT OF PRIORITY

This application is a 35 U.S.C. §371 national phase application of International Application Ser. No. PCT/SE2012/051456, filed Dec. 20, 2012, which claims the benefit, under 35 U.S.C. §119(a), of Swedish Patent Application No. 1151223-3; filed Dec. 20, 2011, the entire contents of which are incorporated by reference herein.

TECHNICAL FIELD

The present disclosure relates to methods and compositions for the inhibition of tumor growth, and particularly to combination compositions and therapies for inhibiting the proliferation of urothelial, colorectal, prostate and breast malignancies in a subject.

BACKGROUND OF THE INVENTION

Prostate, breast, colorectal and urothelial cancers are common cancer forms. Once the cancer has spread, the prognosis is poor. The treatment for all these forms of cancer is radical surgery, hormone therapy, radiations and cytostatic treatment or combination of these.

Avermectins or avermectin compounds represent a group of macrocyclic lactones originally isolated from the fermentation broth of the strain *Streptomyces avermitilis*. Such compounds are currently used as antiparasitic agents and mainly as veterinary medicines. However, the avermectin substance ivermectin (22,23-dihydroavermectin $B_{1a}$+22,23-dihydroavermectin $B_{1b}$) is a known drug also for humans against certain tropical infections with minor or no side effects. It is the therapy of choice based on oral or parenteral administration against a range of nematodes and parasites (Hotson I K. The avermectins: A new family of antiparasitic agents. J S Afr Vet Assoc 1982; 53(2):87-90). The substance ivermectin has previously been described to induce cell death at low micromolar concentrations in acute myeloid leukemia cell lines. However, the exact mechanism of ivermectin remains to be demonstrated.

Sharmeen et al. (The anti-parasitic agent ivermectin induces chloride-dependent membrane hyperpolarization and cell death in leukemia cells, Blood 2010; 116(18): 3593-603) demonstrated a reduction in tumor growth in three independent mouse models of leukemia using concentrations that is pharmacological achievable. Surprisingly the effect on two prostate cancer cell lines was not so pronounced.

Similar to this, Drinyaev et al. (Antitumor effect of avermectins, EUROPEAN JOURNAL OF PHARMACOLOGY, ELSEVIER SCIENCE, NL, vol. 501, no, 1-3, 6 Oct. 2004, p. 19-23), describe an anti-tumor effect on different carcinomatosis models performed in mice. However, no effect was seen without the presence of vincristine, a known and well described alkaloid used for chemotherapy.

Ketoconazole, ibuprofen, diclofenac and celecoxib have been used in experimental studies with tumor cells. Ketoconazole has previously been described to reduce growth of colon adenocarcinoma cells (Kota B P, Allen J D, Roufogalis B D. The effect of vitamin D3 and ketoconazole combination on VDR-mediated P-gp expression and function in human colon adenocarcinoma cells: implications in drug disposition and resistance. Basic Clin Pharmacol Toxicol; 109(2):97-102) and the effect in reduction of tumor growth in the prostate has also been explored (Figg W D, Woo S, Zhu W, Chen X, Ajiboye A S, Steinberg S M, et al. A phase I clinical study of high dose ketoconazole plus weekly docetaxel for metastatic castration resistant prostate cancer. J Urol; 183(6):2219-26.).

Ibuprofen (NSAID) has been described to reduce tumor spread in colorectal cancer (Ruder E H, Laiyemo A O, Graubard B I, Hollenbeck A R, Schatzkin A, Cross A J. Non-steroidal anti-inflammatory drugs and colorectal cancer risk in a large, prospective cohort. Am J Gastroenterol; 106(7): 1340-50).

Diclofenac (NSAID) has been described to decrease the effect on tumor growth in an experimental model in mice with colorectal metastasis.

Celecoxib has previously been described to enhance radiation therapy in human lung cancer and in different tumor cell lines (Kim Y M, Pyo H. Cooperative Enhancement of Radiosensitivity After Combined Treatment of 17-(Allylamino)-17-Demethoxygeldanamycin and celecoxib in Human Lung and Colon Cancer Cell Lines. DNA Cell Biol).

Until today many of the treatment possibilities for patients suffering from cancer diseases result in advanced surgery, or long time treatment with chemotherapy or radiation. The present study demonstrates that the avermectin compounds, alone or in combination with an imidazole antifungal compound and/or a non-steroidal anti-inflammatory drug (NSAID) in micromolar concentrations reduces the cell proliferation rate in five different human tumor cell lines, from four different locations. All cell lines exhibit reduced proliferation rate at 100 micromolar and several of said combinations at even lower concentrations. Using the composition of the invention in the treatment of different human tumor diseases opens up new strategies in cancer treatment.

SUMMARY OF THE INVENTION

Before the present invention is described, it is to be understood that this invention is not limited to the particular embodiments described as such, Methods, devices, and formulations may, of course, vary. It is also to be understood that the terminology used herein is for the purpose of describing particular embodiments only, and is not intended to limit the scope of the present invention which will be limited only by the appended claims. It must be noted that as used herein and in the appended claims, the singular forms "a," "an," and "the" include plural referents unless the context clearly dictates otherwise, and includes reference to equivalent steps and methods known to those skilled in the art.

Furthermore, the terms used in this invention are, in general, expected to adhere to standard definitions generally accepted by those having ordinary skill in the art of chemistry, biochemistry and medicine. A few exceptions, as listed below, have been further defined within the scope of the present invention.

The present studies are based on an observation describing a middle age man suffering from an advanced urothelial cancer with extensive metastasis. Due to a tropical infection (Strongyloidiasis) this patient received the substance ivermectin as a standard treatment dosage. This treated both the tropical infection and surprisingly all the clinical signs of the urothelial cancer disappeared.

Thus, a first aspect of the present invention relates to a composition comprising an avermectin compound in combination with a non-steroidal anti-inflammatory drug (NSAID) and/or an imidazole antifungal compound or suitable pharmaceutically acceptable salts thereof, for use as a medicament.

A second aspect of the present invention relates to a composition comprising an effective amount of an avermectin compound in combination with an effective amount of a non-steroidal anti-inflammatory drug (NSAID) and/or an effective amount of an imidazole antifungal compound, or suitable pharmaceutically acceptable salts thereof, for use in the inhibition of tumor growth and treatment of cancer.

A third aspect of the invention relates to the use of a composition comprising an effective amount of an avermectin compound in combination with an effective amount of a non-steroidal anti-inflammatory drug (NSAID) and/or an effective amount of an imidazole antifungal compound, or suitable pharmaceutically acceptable salts thereof, in the manufacture of a medicament for the inhibition of tumor growth and treatment of cancer.

A fourth aspect of the invention discloses a method for inhibiting growth of tumor cells, comprising contacting the tumor cells with an effective amount of an avermectin compound in combination with an effective amount of a non-steroidal anti-inflammatory drug (NSAID) and/or an effective amount of an imidazole antifungal compound.

A fifth aspect of the present invention relates to a method of inhibiting tumor growth and treating cancer, said method comprising administering to a subject in need thereof a composition comprising an effective amount of an avermectin compound in combination with an effective amount of a non-steroidal anti-inflammatory drug (NSAID) and/or an effective amount of an imidazole antifungal compound, or suitable pharmaceutically acceptable salts thereof.

A sixth aspect of the present invention discloses a kit comprising an effective amount of an avermectin compound and instructions for administering in combination with an effective amount of an imidazole antifungal compound and/or an effective amount of non-steroidal anti-inflammatory drug (NSAID) for use in any of the methods of the invention.

The inventive composition comprises an avermectin compound. When used herein the terms "avermectins" or "avermectin compounds", are used to describe a series of compounds that may be isolated from the fermentation broth of an avermectin-producing strain of *Streptomyces avermitilis*, and derivatives and analogues thereof as well as pharmaceutically acceptable salts and/or prodrugs thereof, or mixtures thereof. There are eight major natural avermectin compounds, designated A1a, A1b, A2a, A2b, B1a, B1b, B2a and B2b. These designations are based on the structure of the Formula I below and variations of individual compounds as shown in the following table 1.

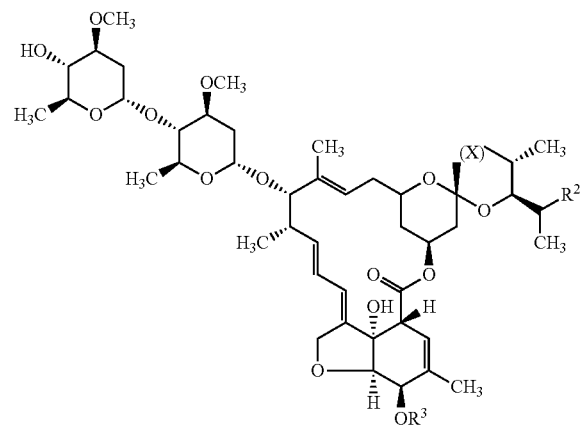

(I)

TABLE 1

| Compound | X | $R^1$ | $R^2$ |
|---|---|---|---|
| A1a | —CH=CH— | $CH_3$ | $C_2H_5$ |
| A1b | —CH=CH— | $CH_3$ | $CH_3$ |
| A2a | —$CH_2$CH(OH)— | $CH_3$ | $C_2H_5$ |
| A2b | —$CH_2$CH(OH)— | $CH_3$ | $CH_3$ |
| B1a | —CH=CH— | H | $C_2H_5$ |
| B1b | —CH=CH— | H | $CH_3$ |
| B2a | —$CH_2$CH(OH)— | H | $C_2H_5$ |
| B2b | —$CH_2$CH(OH)— | H | $CH_3$ |

The avermectins are generally isolated as mixtures of the "a" and "b" components (typically >80% "a" and <20% "b"). Such compounds differ only in the nature of the $R^2$ substituent and this minor structural difference has been found to have little effect on the chemical reactivity or biological activity of the compounds. Thus, although the "a" and "b" components can be separated from each other by chromatography this is not necessary and hence is not normally done. The presence of a mixture of "a" and "b" components may be indicated by dropping the "a" or "b" from the designation of the compound. A mixture of avermectin B1a and avermectin B1b is thus referred to as avermectin B1. Alternatively, a slash (/) is inserted between the compound designations to indicate a mixture such as in "B1a/B1b".

The avermectins may also be made synthetically (see Avermectin aglycons. Helmut Mrozik, Philip Eskola, Byron H. Arison, George Albers-Schoenberg, Michael H. Fisher J. Org. Chem., 1982, 47 (3), pp 489-92; Ivermectin-derived leishmanicidal compounds, Falcao C A, Muzitano M F, Kaiser C R, Rossi-Bergmann B, Ferezou J P. Bioorg Med Chem. 2009 Jan. 15; 17(2):496-502). Examples of synthetic derivatives or analogues of avermectins defined in the art are ivermectin, doramectin, eprinomectin and selamectin. Some of these avermectins are products made synthetically starting from avermectins isolated from the above fermentation broth, e.g. by chemical reduction of one double bond to form ivermectin, or other series of chemical reactions to form other avermectins. The above avermectins may be used as antiparasitic and anti-bacterial agents.

The term "avermectin" includes, in particular the compounds avermectin, ivermectin, abamectin, doramectin, eprinomectin and selamectin, and mixtures and/or solvates thereof. Thus, the avermectin compound of the invention is selected from the group consisting of the compounds ivermectin, invermectin, avermectin, abamectin, doramectin, epinomectin and selamectin.

The avermectin compound is selected from the group consisting of ivermectin ((22,23-dihydroavermectin $B_{1a}$+ 22,23-dihydroavermectin $B_{1b}$)), abamectin (mixture of (10E,14E,16E)-(1R,4S,5'S,6S,6'R,8R,12S,13S,20R,21R, 24S)-6'-[(S)-sec-butyl]-21,24-dihydroxy-5',11,13,22-tetramethyl-2-oxo-(3,7,19-trioxatetracyclo[15.6.1.14,8.020, 24]pentacosa-10,14,16,22-tetraene)-6-spiro-2'-(5',6'-dihydro-2'H-pyran)-12-yl 2,6-dideoxy-4-O-(2,6-dideoxy-3-O-methyl-α-L-arabino-hexopyranosyl)-3-O-methyl-α-L-arabino-hexopyranoside and (10E,14E,16E)-(1R,4S,5'S,6S, 6'R,6R,8R12S,13S,20R,21R,24S)-21,22-dihydroxy-6'-isopropyl-5',11,13,22-tetramethyl-2-oxo-(3,7,19-trioxatetracyclo[15.6.1.14,8.020,24]pentacosa-10,14,16,22-tetraene)-6-spiro-2'-(5',6'-dihydro-2'H-pyran)-12-yl 2,6-dideoxy-4-O-(2,6-dideoxy-3-O-methyl-α-L-arabino-hexopyranosyl)-3-O-methyl-α-L-arabino-hexopyranoside), doramectin ((1'R,2S,4'S,5S,6R,8'R,10'E,12'R,13'S, 14'E, 20'R,21'R,24'S)-6-cyclohexyl-21',24'-dihydroxy-12'-{[(2R, 4S,5S,6S)-5-{[(2S,4S,5S,6S)-5-hydroxy-4-methoxy-6-methyloxan-2-yl]oxy}-4-methoxy-6-methyloxan-2-yl]oxy}-5,11',13',22'-tetramethyl-5,6-dihydro-3',7',19'-trioxaspiro[pyran-2,6'-tetracyclo[15.6.1.1$^{4,8}$.0$^{20,24}$]pentacosane]-10',14',16',22'-tetraen-2'-one), eprinomectin (mixture of (10E,14E,16E)-(1R,4S,5'S,6S,6'R,8R,12S,13S,20R,21R,24S)-6'-[(S)-sec-butyl]-21,24-dihydroxy-5',11,13,22-tetramethyl-2-oxo-(3,7,19-trioxatetracyclo[15.6.1.1$^{4,8}$.0$^{20,24}$]pentacosa-10,14,16,22-tetraene)-6-spiro-2'-(5',6-dihydro-2'H-pyran)-12-yl 4-O-(4-acetamido-2,4,6-trideoxy-3-O-methyl-α-L-lyxo-hexopyranosyl)-2,6-dideoxy-3-O-methyl-α-L-arabino-hexopyranoside (major component) and (10E,14E,16E)-(1R,4S,5'S,6S,6'R,8R,12S,13S,20R,21R,24S)-21,24-dihydroxy-6'-isopropyl-5',11,13,22-tetramethyl-2-oxo-(3,7,19-trioxatetracyclo[15.6.1.1$^{4,8}$.0$^{22,24}$]pentacosa-10,14,16,22-tetraene)-6-spiro-2'-(5',6'-dihydro-2'H-pyran)-12-yl 4-O-(4-acetamido-2,4,6-trideoxy-3-O-methyl-α-L-lyxo-hexopyranosyl)-2,6-dideoxy-3-O-methyl-α-L-arabino-hexopyranoside (minor component)) and selamectin ((10E,14E,16E,21Z)-(1R,4S,5'S,6R,6'S,8R,12S,13S,20R,21R,24S)-6'-cyclohexyl-24-hydroxy-21-hydroxylimino-5',11,13,22-tetramethyl-2-oxo-(3,7,19-trioxatetracyclo[15.6.1.1$^{4,8}$.0$^{22,24}$]pentacosa-10,14,16,22-tetraene)-6-spiro-2'-(tetrahydropyran)-12-yl 2,6-dideoxy-3-O-methyl-α-L-arabino-hexopyranoside).

The avermectin compound is advantageously one of ivermectin, abamectin or selamectin.

The avermectin compound is advantageously abamectin or selamectin.

The avermectin compound may be ivermectin.

The avermectin compound may be abamectin.

The avermectin compound may be selamectin.

The composition of the invention further comprises a non-steroidal anti-inflammatory drug (NSAID) and/or an imidazole antifungal compound. It should be pointed out that the term "and/or" as used herein is meant to indicate that the listed options are either present together or individually. For example, the composition of the invention includes a compound of the avermectin compound and a NSAID compound, or a compound of the imidazole antifungals. Alternatively the composition may include an avermectin compound and a NSAID compound and an imidazole antifungal compound.

The term "non-steroidal anti-inflammatory drugs (NSAID)" refers to a group of drugs with analgesic and antipyretic (fever-reducing) effects and which have, in higher doses, anti-inflammatory effects. They are usually indicated for the treatment of acute or chronic conditions where pain and inflammation are present. Prostaglandins act for example as messenger molecules in the process of inflammation.

The non-steroidal anti-inflammatory drug (NSAID) maybe selected from the group of compounds consisting of salicylates, propionic acids, acetic acids, enolic acids, fenamic acid, selective COX-2 inhibitors and sulphonanilides.

The salicytates may be selected from the group consisting of aspirin (2-acetoxybenzoic acid). Diflunisal (2',4'-difluoro-4-hydroxybiphenyl-3-carboxylic acid), and salsalate (2-(2-Hydroxybenzoyl)oxybenzoic acid).

The propionic acid derivative may be selected from the group consisting of ibuprofen ((RS)-2-(4-(2-methylpropyl)phenyl)propanoic acid), naproxen ((+)-(S)-2-(6-methoxynaphthalen-2-yl)propanoic acid), fenoprofen (2-(3-phenoxyphenyl)propanoic acid), Ketoprofen (RS)-2-(3-benzoylphenyl)propanoic acid), flurbiprofen ((RS)-2-(2-fluorobiphenyl-4-yl)propanoic acid), oxaprozin (3-(4,5-dphenyl-1,3-oxazol-2-yl)propanoic acid), and loxoprofen ((RS)-2-{4-[(2-oxocyclopentyl)methyl]phenyl}propanoic acid).

The acetic acid derivative may be selected from the group consisting of indomethacin (2-{1-[(4-chlorophenyl)carbonyl]-5-methoxy-2-methyl-1H-indol-3-yl}acetic acid), sulindac ({(1Z)-5-fluoro-2-methyl-1-[4-(methylsulfinyl)benzylidene]-1H-indene-3-yl}acetic acid), etodolac ((RS)-2-(1,8-Diethyl-4,9-dihydro-3H-pyrano[3,4-b]indol-1-yl)acetic acid), ketorolac ((±)-5-benzoyl-2,3-dihydro-1H-pyrrolizine-1-carboxylic acid, 2-amino-2 -(hydroxymethyl)-1,3-propanediol), diclofenac (2-(2-(2,6-dichlorophenylamino)phenyl)acetic acid), and nabumetone (4-(6-methoxy-2-naphthyl)-2-butanone).

The enolic acid (Oxicam) derivative may be selected from the group consisting of piroxicam ((8E)-8-[hydroxy-(pyridin-2-ylamino)methylidene]-9-methyl-10,10-dioxo-10λ$^6$-thia-9-azabicyclo[4.4.0]deca-1,3,5-trien-7-one), meloxicam (4-hydroxy-2-methyl-N-(5-methyl-2-thiazolyl)-2H-1,2-benzothiazine-3-carboxamide-1,1-dioxide), tenoxicam ((3E)-3-[hydroxy(pyridin-2-ylamino)methylene]-2-methyl-2,3-dihydro-4H-thieno[2,3-e][1,2]thiazin-4-one 1,1-dioxide), droxicam (2H,5H-1,3-Oxazino(5,6-c)(1,2)benzothiazine-2,4(3H)-dione, 5-methyl-3-(2-pyridinyl)-, 6,6-dioxide), lomoxicam ((3E)-6-chloro-3-[hydroxy(pyridin-2-ylamino)methylene]-2-methyl-2,3-dihydro-4H-thieno[2,3-e][1,2]thiazin-4-one 1,1-dioxide), and isoxicam.

The fenamic acid derivative (fenamates) may be selected from the group consisting of mefenamic acid (2-(2,3-dimethylphenyl)aminobenzoic acid), meclofenamic acid (2[(2,6-dichloro-3-methylphenyl)amino]benzoic acid), flufenamic acid (2-{[3-(Trifluoromethyl)phenyl]amino}benzoic acid) and tolfenamic acid (2-[(3-chloro-2-methylphenyl)amino]benzoic acid)).

The selective COX-2 inhibitor (Coxibs) may be selected from the group consisting of celecoxib (4-[5-(4-methylphenyl)-3-(trifluoromethyl)pyrazol-1-yl]benzenesulfonamide), rofecoxib (4-(4-methylsulfonylphenyl)-3-phenyl-5H-furan-2-one), valdecoxib (4-(5-methyl-3-phenylisoxazol-4-yl)benzenesulfonamide), parecoxib (N-{[4-(5-methyl-3-phenylisoxazol-4-yl)phenyl]sulfonyl}propanamide), lumiracoxib ({2-[(2-chloro-6-fluorophenyl)amino]-5-methylphenyl}acetic acid), etoricoxib (5-chloro-6'-methyl-3-[4-(methylsulfonyl)phenyl]-2,3'-bipyridine), and firocoxib (3-(Cyclopropylmethoxy)-5,5-dimethyl-4-(4-methylsulfonylphenyl)furan-2-one).

The sulphonanilide may be nimesulide (N-(4-Nitro-2-phenoxyphenyl)methanesulfonamide).

Advantageously the NSAID compound is ibuprofen, diclofenac, or celecoxib.

The NSAID compound may be ibuprofen.

The NSAID compound may be diclofenac.

The NSAID compound may be celecoxib.

As used herein the term "Imidazole antifungal compound" is intended to encompass a group of compounds with action against fungi and some gram-positive bacteria. The group of imidazole antifungal compounds include compounds selected from the group consisting of miconazole (trade name Micatin or Daktarin), ketoconazole (trade names Nizoral, Fungoral and Sebizole), clotrimazole (trade names Lotrimin, Lotrimin AF and Canesten), albendazole, econazole, omoconazole, bifonazole, butoconazole, fenticonazole, isoconazole, oxiconazole, sertaconazole (trade name Ertaczo), sulconazole, tioconazole.

The imidazole antifungal compound to be used in the composition of the present invention may be selected from the group consisting of miconazole ((RS)-1-(2-(2,4-Dichlorobenzyloxy)-2-(2,4-dichlorophenyl)ethyl)-1H-imidazole), ketoconazole (1-[4-(4-{[(2R,4S)-2-(2,4-Dichlorophenyl)-2-(1H-imidazol-1-ylmethyl)-1,3-dioxolan-4-yl]methoxy}phenyl)piperazin-1-yl]ethan-1-one), clotrimazole (1-[(2-chlorophenyl)(diphenyl)methyl]-1H-imidazole), econazole ((RS)-1-{2-[(4-chlorophenyl)methoxy]-2-(2,4-dichlorophenyl)ethyl}-1H-imidazole), omoconazole (1-[(Z)-2-[2-(4-chlorophenoxy)ethoxy]-2-(2,4-dichlorophenyl)-1-methylvinyl]-1H-imidazole), bifonazole ((RS)-1-[phenyl(4-phenylphenyl)methyl]-1H-imidazole), butoconazole (1-[4-(4-chlorophenyl)-2-(2,6-dichlorophenyl)sulfanylbutyl]imidazole), fenticonazole (1-[2-(2,4-dichlorophenyl)-2-{[4-(phenylsulfanyl)phenyl]methoxy}ethyl]-1H-imidazole), isoconazole ((RS)-1-[2-[(2,6-Dichlorobenzyl)oxy]-2-(2,4-dichlorophenyl)ethyl]-1H-imidazole), oxiconazole ((E)-[1-(2,4-dichlorophenyl)-2-(1H-imidazol-1-yl)ethylidene][(2,4-dichlorophenyl)methoxy]amine), sertaconazole (1-{2-[(7-chloro-1-benzothiophen-3-yl)methoxy]-2-(2,4-dichlorophenyl)ethyl}-1H-imidazole), albendazole (Methyl[6-(propylthio)-1H-benzoimidazol-2-yl]carbamate), sulconazole (1-(2-{[(4-chlorophenyl)methyl]sulfanyl}-2-(2,4-dichlorophenyl)ethyl)-1H-imidazole), and tioconazole ((RS)-1-(2-[(2-Chloro-3-thienyl)methoxy-2-(2,4-dichlorophenyl)ethyl]-1H-imidazole). Advantageously the imidazole antifungal compound is ketoconazole or albendazole.

The imidazole antifungal compound may be ketoconazole.

The imidazole antifungal compound may be albendazole.

It should be pointed out that certain compounds of the present invention may as listed above exist as tautomers or stereoisomers (e.g. racemate, enantiomer, diastereomer or E- or Z-isomer). It is to be understood that the present invention encompasses all such tautomers or stereoisomers.

Certain compounds of the present invention may exist as solvates or hydrates. It is to be understood that the present invention encompasses all such solvates or hydrates.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "pharmaceutically acceptable" as used herein means compatible with the treatment of animals, in particular, humans. The term "pharmaceutically acceptable salt" means an acid addition salt which is suitable for or compatible with the treatment of patients. A "suitable pharmaceutically acceptable salt" of a compound of the invention is, for example, an acid-addition salt of a compound of the invention which is sufficiently basic, for example, an acid-addition salt with, for example, an inorganic or organic acid, for example hydrochloric, hydrobromic, nitric, methanesulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a "suitable pharmaceutically acceptable salt" of a compound of the invention, is, for example, a base-addition salt of a compound of the invention which is sufficiently acidic, for example, a metal salt, for example sodium, potassium, calcium, magnesium, zinc or aluminum, an ammonium salt, a salt with an organic base which affords a physiologically acceptable cation, which includes quartenery ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (IR, 2S)-2-hydroxyinden-I-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine.

For clarity, when a compound is referred to by its chemical name, unless otherwise indicated, this reference includes salts (where applicable), solvates and/or prodrugs of the compound. In an embodiment, when a compound is referred to by its chemical name, unless otherwise indicated, this reference includes salts (where applicable), and/or solvates of the compound.

The composition of the invention should comprise an effective amount of the mentioned compounds. As used herein, the phrases "effective amount", "therapeutically effective amount" or term "pharmacologically effective amount" mean an amount effective, at dosages and for periods of time necessary to achieve the desired result. For example in the context of inhibiting a tumor growth, an effective amount is an amount that for example induces remission, reduces tumor burden, and/or prevents tumor spread or growth compared to the response obtained without administration of the compound. Effective amounts may vary according to factors such as the disease state, age, sex, weight of the subject. The amount of a given compound that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art.

The composition of the invention is advantageously used in the inhibition of tumor growth and treatment of cancer. As used herein the term "cancer" refers to a physical condition in mammals that is typically characterized by a group of cells that display uncontrolled growth (division beyond the normal limits), invasion (intrusion on and destruction of adjacent tissues), and sometimes metastasis (spread to other locations in the body via lymph or blood). Examples of cancers include but are not limited to breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, brain cancer, and/or metastasis thereof. The cancer can be any of the above-mentioned types of cancer but especially the cancer types urothelial cell carcinoma, colon cancer, prostate cancer and breast cancer.

When used herein the term "carcinoma" means cancers derived from epithelial cells. This group includes many of the most common cancers, particularly in the aged, and include nearly all those developing in the breast, prostate, lung, pancreas, and colon.

When used herein the term "urothelial cell carcinoma (UCC)" also transitional cell carcinoma (TCC), is intended to mean a type of cancer that typically occurs in the urinary system: the kidney, urinary bladder, and accessory organs. Urothelial carcinoma accounts for about 90% of all bladder cancers (including cancer of the ureter, urethra, and urachus) and begins in the urothelium. It is the second most common type of kidney cancer, but accounts for only 5% to 10% of all primary renal malignant tumors. A tumor of this type may be described further using one of the four subcategories explained below, all of which are encompassed in the term urothelial cell cancer.

Non-muscle-invasive/superficial urothelial carcinoma is a subtype of urothelial carcinoma located only in the urothelium and is non-muscle-invasive, meaning it has not invaded the muscle layer. It may invade the lamina propria beneath the transitional cells. This is sometimes called invasive, though it is not the deeply invasive type that can spread to the muscle layer.

Muscle-invasive urothelial carcinoma (often called invasive urothelial carcinoma) is a subtype of urothelial carcinoma that spreads to the bladder's muscularis propria and sometimes to the fatty layers or surrounding tissue outside the muscle.

Papillary urothelial carcinoma. Papillary is a word that describes a growth that is like a small polyp or flower-shaped cluster of cancer cells. A noninvasive papillary tumor grows into the hollow center of the bladder on a stalk. Invasive papillary urothelial carcinoma can spread into the lamina propria or muscle layer.

Flat urothelial carcinoma. Noninvasive flat urothelial carcinoma (also called carcinoma in situ, or CIS) grows in the layer of cells closest to the inside of the bladder and appears as flat lesions on the inside surface of the bladder. Invasive flat urothelial carcinoma may invade the deeper layers of the bladder, particularly the muscle layer.

Squamous cell carcinoma. This type accounts for about 4% of all bladder cancers and starts in squamous cells, which are thin, flat cells.

Adenocarcinoma. This type accounts for about 2% of all bladder cancers and begins in glandular cells.

All major types of bladder cancer can metastasize (spread) beyond the bladder. If the tumor has spread into the surrounding organs (the uterus and vagina in women, the prostate in men, and/or nearby muscles), it is called locally advanced disease. Bladder cancer can also often spread to the lymph nodes in the pelvis. If it has spread into the liver, bones, lungs, lymph nodes outside the pelvis, or other parts of the body, these are distant metastases and the cancer is called metastatic or advanced disease.

Included in the term "urothelial cancer" are also other, less common types of cancer that begin in the bladder, including sarcoma (which begins in the muscle layers of the bladder) and small cell anaplastic cancer (a rare type of bladder cancer that is likely to spread to other parts of the body).

When used herein the term "Colorectal cancer" or "bowel cancer", is intended to mean a cancer caused by uncontrolled cell growth (neoplasia), in the colon, rectum, or vermiform appendix. Colorectal cancer is clinically distinct from anal cancer, which affects the anus.

Colorectal cancers start in the lining of the bowel, and if left untreated, it can grow into the muscle layers underneath, and then through the bowel wall. Most begin as a small growth on the bowel wall: a colorectal polyp or adenoma. These mushroom-shaped growths are usually benign, but some develop into cancer over time. Localized bowel cancer is usually diagnosed through colonoscopy.

Invasive cancers that are confined within the wall of the colon (TNM stages I and II) are often curable with surgery. However, if left untreated, the cancer can spread to regional lymph nodes (stage III). Cancer that has spread widely around the body (stage IV) is usually not curable. The most common colon cancer cell type is adenocarcinoma which accounts for 95% of cases. Other, rarer types include lymphoma and squamous cell carcinoma.

When used herein the term "prostate cancer" is intended to mean a form of cancer that develops in the prostate, a gland in the male reproductive system. Most prostate cancers are slow growing; however, there are cases of aggressive prostate cancers. Prostate cancer is classified as an adenocarcinoma, or glandular cancer. The cancer cells may metastasize from the prostate to other parts of the body, particularly the bones and lymph nodes. Prostate cancer may cause pain, difficulty in urinating, problems during sexual intercourse, or erectile dysfunction. Other symptoms can potentially develop during later stages of the disease.

Prostate cancer tends to develop in men over the age of fifty and although it is one of the most prevalent types of cancer in men, many never have symptoms, undergo no therapy, and eventually die of other causes. About two-thirds of cases are slow growing, the other third more aggressive and fast developing.

When used herein the term "breast cancer (malignant breast neoplasm)" is cancer originating from breast tissue, most commonly from the Inner lining of milk ducts or the lobules that supply the ducts with milk. Cancers originating from ducts are known as ductal carcinomas; those originating from lobules are known as lobular carcinomas. Breast cancer is a disease of humans and other mammals; while the overwhelming majority of cases in humans are women, men can also develop breast cancer. Breast cancers are classified by several grading systems. Each of these influences the prognosis and can affect treatment response. Description of a breast cancer optimally includes all of these factors.

Histopathology. Breast cancer is usually classified primarily by its histological appearance. Most breast cancers are derived from the epithelium lining the ducts or lobules, and these cancers are therefore classified as ductal or lobular carcinoma. Carcinoma in situ is growth of low grade cancerous or precancerous cells within a particular tissue compartment such as the mammary duct without invasion of the surrounding tissue. In contrast, invasive carcinoma does not confine itself to the initial tissue compartment.

Grade. Grading compares the appearance of the breast cancer cells to the appearance of normal breast tissue. Normal cells in an organ like the breast become differentiated, meaning that they take on specific shapes and forms that reflect their function as part of that organ. Cancerous cells lose that differentiation. In cancer, the cells that would normally line up in an orderly way to make up the milk ducts become disorganized. Cell division becomes uncontrolled. Cell nuclei become less uniform. Pathologists describe cells as well differentiated (low grade), moderately differentiated (intermediate grade), and poorly differentiated (high grade) as the cells progressively lose the features seen in normal breast cells. Poorly differentiated cancers have a worse prognosis.

Stage. Breast cancer staging using the TNM system is based on the size of the tumor (T), whether or not the tumor has spread to the lymph nodes (N) in the armpits, and whether the tumor has metastasized (M) (i.e. spread to a more distant part of the body). Larger size, nodal spread, and metastasis have a larger stage number and a worse prognosis.

The main stages in breast cancer are:
Stage 0 is a pre-cancerous or marker condition, either ductal carcinoma in situ (DCIS) or lobular carcinoma in situ (LCIS).
Stages 1-3 are within the breast or regional lymph nodes.
Stage 4 is 'metastatic' cancer that has a less favorable prognosis.

Receptor status. Breast cancer cells have receptors on their surface and in their cytoplasm and nucleus. Chemical messengers such as hormones bind to receptors, and this causes changes in the cell. Breast cancer cells may or may not have three important receptors: estrogen receptor (ER), progesterone receptor (PR), and HER2/neu.

ER+ cancer cells depend on estrogen for their growth, so they can be treated with drugs to block estrogen effects (e.g. tamoxifen), and generally have a better prognosis.

HER2+ breast cancer has a worse prognosis, but HER2+ cancer cells respond to drugs such as the monoclonal antibody trastuzumab (in combination with conventional chemotherapy), and this has improved the prognosis significantly. Cells with none of these receptors are called basal-like or triple negative.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total, including cured), whether detectable or undetectable. "Treating" and "Treatment" can also mean prolonging survival as compared to expected survival if not receiving treatment. "Treating" and "treatment" as used herein also include prophylactic treatment. For example, a subject with early tumor disease can be treated to inhibit growth of a tumor, and thereby prevent progression of tumor growth or alternatively a subject in remission can be treated with a compound or composition described herein to prevent recurrence.

The compositions of the present invention, comprising any of the combinations of compounds as described above are particularly useful for inhibiting growth of tumors and treating cancers of the group consisting of urothelial cancer, colorectal cancer, prostate cancer and breast cancer. Such a composition is therefore advantageously used in a method for inhibiting tumor growth, as well as treating cancers of the group consisting of urothelial cancer, colorectal cancer, prostate cancer and breast cancer, said method comprising administering the above combination of compounds to a subject in need thereof.

The composition of the invention is advantageously used in the inhibition of tumor growth and treatment of urothelial cell carcinoma.

The composition of the invention is advantageously used in the inhibition of tumor growth and treatment of colon cancer.

The composition of the invention is advantageously used in the inhibition of tumor growth and treatment of prostate cancer.

The composition of the invention is advantageously used in the inhibition of tumor growth and treatment of breast cancer.

As used herein the term "subject" refers to a living animal or human in need of treatment for, or susceptible to, a condition involving a tumor disease. The term subject includes, but is not limited to, humans, nonhuman primates such as chimpanzees and other apes and monkey species, farm animals such as cattle, sheep, pigs, goats and horses, domestic mammals such as dogs and cats, laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

Thus, treatment methods comprise administering to a subject a therapeutically effective amount of a combination of compounds or composition comprising the combination of compounds described herein and optionally consists of a single administration, or alternatively comprises a series of applications. For example, the composition described herein may be administered at least once a week. However, in another embodiment, the composition may be administered to the subject from about one time per week to about once daily for a given treatment. In another embodiment, the composition is administered twice daily. The length of the treatment period depends on a variety of factors, such as the severity of the disease, the age of the patient, the concentration, the activity of the compounds of the composition described herein, and/or a combination thereof. It will also be appreciated that the effective dosage of the composition used for the treatment or prophylaxis may increase or decrease over the course of a particular treatment or prophylaxis regime. Changes in dosage may result and become apparent by standard diagnostic assays known in the art. In some instances, chronic administration may be required. For example, the composition is administered to the subject in an amount and for a duration sufficient to treat the patient.

The composition of the invention may be administered contemporaneously to a subject in need thereof. As used herein, "contemporaneous administration" and "administered contemporaneously" means that the avermectin compound (e.g. ivermectin, abamectin and or selamectin) and NSAID and/or an imidazole antifungal compound are administered to a subject such that they are each biologically active in the subject at the same time. The exact details of the administration will depend on the pharmacokinetics of the substances in the presence of each other, and can include administering one substance within 24 hours of administration of another, if the pharmacokinetics is suitable. Designs of suitable dosing regimens are routine for one skilled in the art. In particular embodiments, two substances will be administered substantially simultaneously, i.e. within minutes of each other, or in a single composition that comprises both substances.

The composition of the invention may be administered as a combination therapy to a subject in need thereof. The terms "combination therapy" or "in combination with" as used herein mean that two or more substances, for example the avermectin compound (e.g. ivermectin, abamectin or selamectin) and a NSAID and/or an imidazole antifungal compound, are administered to a subject over a period of time, contemporaneously or sequentially e.g. the substances are administered at the same time or at different times within the period of time in a regimen that will provide beneficial effects of the drug combination, at similar or different intervals. For example, the combination therapy is intended to embrace co-administration, in a substantially simultaneous manner such as in a single capsule having a fixed ratio of active ingredients or in multiple, separate capsules for each substance. The compounds may or may not be biologically active in the subject at the same time. As an example, a first substance is administered weekly, and a second substance administered every other week for a number of weeks. The exact details of the administration will depend on the pharmacokinetics of the substances. Designs of suitable dosing regimens are routine for one skilled in the art. As used herein, the phrase "dosage form" refers to the physical form of a dose for example comprising compounds of the disclosure, and includes without limitation tablets, including enteric coated tablets, caplets, gelcaps, capsules, ingestible tablets, buccal tablets, troches, elixirs, suspensions, syrups, wafers, liposomal formulations and the like. The dosage form may be solid or liquid, cold, ambient or warm. Liposomal formulations can for example be used to administer multiple compounds at fixed ratios.

The compounds of the present invention can be administered alone or in oral dosage forms as tablets, capsules (each including timed release and sustained release formulations), pills, powders, granules, elixirs, tinctures, suspensions, syrups and emulsions. Likewise, they may also be administered in intravenous form (both bolus and infusion), intraperitoneal, subcutaneous or intramuscular form, all using forms well known to those of ordinary skill in the pharmaceutical arts. An effective but non-lethal amount of the compounds desired can be employed as an antitumor agent. Thus, the avermectin compound in combination with non-steroidal anti-inflammatory drug (NSAID), and/or an imidazole antifungal compound should be administered in amounts that together inhibit tumor growth.

The dosage regimen utilizing the compounds of the present invention is selected in accordance with a variety of factors including type, species, age, weight, sex and medical condition of the subject; the severity of the condition to be treated; the route of administration; the renal and hepatic function of the subject; and the particular compound or salt thereof employed. An ordinarily skilled physician or veterinarian can readily determine and prescribe the effective amount of the drug required.

Dosages of the present invention, when used for the indicated effects, will for Ivermectin range from 0.0001-8 mg/kg bodyweight, more preferably between 0.0002-4 mg/kg bodyweight, and most preferably 0.0004-2 mg/kg bodyweight, for Selamectin: 0.0001-8 mg/kg bodyweight, more preferably between 0.0002-4 mg/kg bodyweight and most preferably about 0.0004-2 mg/kg bodyweight, for Abamectin: about 0.00001-8 mg/kg bodyweight, more preferably between 0.00002-4 mg/kg bodyweight, and most preferably about 0.00004-2 mg/kg bodyweight; for Ketoconazole: about 0.01-70 mg/kg bodyweight; more preferably between 0.02-40 mg/kg bodyweight, and most preferably about 0.03-30 mg/kg bodyweight; for Albendazole: about 0.01-60 mg/kg bodyweight, more preferably between 0.02-30 mg/kg bodyweight, most preferably about 0.03-25 mg/kg bodyweight; Ibuprofen: about 0.01-70 mg/kg bodyweight, more preferably between 0.02-40 mg/kg bodyweight, most preferably about 0.03-30 mg/kg bodyweight; for Celecoxib about 0.01-30 mg/kg bodyweight, more preferably between 0.02-15 mg/kg bodyweight, most preferably about 0.03-12 mg/kg bodyweight; for Diklofenac about 0.01-5 mg/kg bodyweight, more preferably 0.02-4 mg/kg bodyweight, most preferably about 0.03-3 mg/kg bodyweight.

Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as *acacia*, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers or hydrogels.

It is demonstrated herein that avermectin compounds, and in particular ivermectin, selamectin or abamectin, when used alone reduces the cell proliferation rate in micromolar concentrations in vitro in five different human tumor cell lines (urinary, colorectal, prostate and breast tumor cell lines), from four different locations.

However, when ivermectin, selamectin or abamectin is combined with ibuprofen and/or celecoxib and/or diclofenac all NSAID and/or, ketoconazole or albendazole imidazole antifungal compounds, surprising synergistic effects in the reduction of this proliferation rate are provided. The term "synergistic" as used herein means the enhanced or magnified effect of a combination on at least one property compared to the additive individual effects of each component of the combination. For example, compounds that induce cell death by the same mechanism would not be expected to have more than additive effect. The term "cell death" as used herein includes all forms of cell death including necrosis and apoptosis.

Therefore, the composition of the invention may comprise any one of the following combinations of compounds: ivermectin+ketoconazole; ivermectin+ketoconazole+ibuprofen; ivermectin+ketoconazole+diclofenac; ivermectin+ketoconazole+celecoxib; ivermectin+albendazole; ivermectin+albendazole+ibuprofen; ivermectin+albendazole+diclofenac; ivermectin+albendazole+celecoxib; ivermectin+ibuprofen; ivermectin+diclofenac; ivermectin+celecoxib; abamectin+ketoconazole; abamectin+ketoconazole+ibuprofen; abamectin+ketoconazole+diclofenac; abamectin+ketoconazole+celecoxib; abamectin+albendazole; abamectin+albendazole+ibuprofen; abamectin+albendazole+diclofenac; abamectin+albendazole+celecoxib; abamectin+ibuprofen; abamectin+diclofenac; abamectin+celecoxib; selamectin+ketoconazole; selamectin+ketoconazole+ibuprofen; selamectin+ketoconazole+diclofenac; selamectin+ketoconazole+celecoxib; selamectin+albendazole; selamectin+albendazole+ibuprofen; selamectin+albendazole+diclofenac; selamectin+albendazole+celecoxib; selamectin+ibuprofen; selamectin+diclofenac or selamectin+celecoxib and may advantageously be used for inhibiting growth of tumors and treating cancers of the group consisting of urothelial cancer, colorectal cancer, prostate cancer and/or breast cancer.

Still a further aspect of the present invention discloses a kit comprising an effective amount of an avermectin compound and instructions for administering in combination with an effective amount of a non-steroidal anti-inflammatory drug (NSAID) and/or an imidazole antifungal compound an effective amount of for use in any of the methods of the invention.

As mentioned above it has been demonstrated herein that avermectin compounds, and in particular ivermectin, selamectin or abamectin, when used alone reduces the cell proliferation rate in micromolar concentrations in vitro in five different human tumor cell lines (urinary, colorectal, prostate and breast tumor cell lines), from four different locations. Therefore, one further aspect of the present invention also provides a composition comprising an effective amount of an avermectin compound or suitable pharmaceutically acceptable salt thereof, for use in the inhibition of tumor growth and treatment of cancer. Said composition comprising an effective amount of an avermectin compound or suitable pharmaceutically acceptable salt thereof, may be used for the manufacture of a medicament for the inhibition of tumor growth and treatment of cancer.

A further aspect of the present invention provides a use of a composition comprising an effective amount of anyone of the avermectins ivermectin, selamectin or abamectin or suitable pharmaceutically acceptable salts thereof, for inhibiting growth of tumors and treating cancers of the group consisting of urothelial cancer, colorectal cancer, prostate cancer and/or breast cancer.

A further aspect of the invention also provides a method of inhibiting tumor growth and treating cancer, said method comprising administering to a subject in need thereof a composition comprising an effective amount of an avermectin compound or suitable pharmaceutically acceptable salt thereof.

The composition may advantageously comprise an effective amount of ivermectin or suitable pharmaceutically acceptable salt thereof, for use in the inhibition of tumor growth and treatment of cancer.

The composition may advantageously comprise an effective amount of selamectin or suitable pharmaceutically acceptable salt thereof, for use in the inhibition of tumor growth and treatment of cancer.

The composition may advantageously comprise an effective amount of abamectin or suitable pharmaceutically acceptable salt thereof, for use in the inhibition of tumor growth and treatment of cancer.

The composition comprising an effective amount of anyone of the avermectins ivermectin, selamectin or abamectin or suitable pharmaceutically acceptable salts thereof, may advantageously be used for the inhibition of tumor growth and treatment of urothelial cell carcinoma.

The composition comprising an effective amount of anyone of the avermectins ivermectin, selamectin or abamectin or suitable pharmaceutically acceptable salts thereof, may advantageously be used for the inhibition of tumor growth and treatment of colon cancer.

The composition comprising an effective amount of anyone of the avermectins ivermectin, selamectin or abamectin or suitable pharmaceutically acceptable salts thereof, may advantageously be used for the inhibition of tumor growth and treatment of prostate cancer.

The composition comprising an effective amount of anyone of the avermectins ivermectin, selamectin or abamectin or suitable pharmaceutically acceptable salts thereof, may advantageously be used for the inhibition of tumor growth and treatment of breast cancer.

DETAILED DESCRIPTION OF THE INVENTION

In the following examples the invention will be described in more detail. However, the described embodiments mentioned below are only given as examples and should not be limiting to the present invention. Other solutions, uses, objectives, and functions within the scope of the invention as claimed in the below described patent claims should be apparent for the person skilled in the art.

EXAMPLES AND DESCRIPTION OF TEST METHODS

Materials

If not other stated all chemicals and cell culture reagents were purchased from Sigma-Aldrich (St Louis, Mo., USA).

Cell Culture

Figure 1:
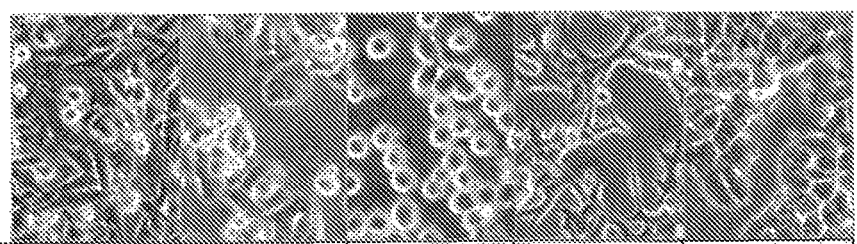
FIG. 1 shows properties and micrographs of human tumor cells used in the present study.

Commercially available human tumor cell lines were purchased from ATCC (ATCC/LGC-standards, Borás, Sweden). Cell lines from urinary bladder (UM-UC-3, #CRL-1749), colorectal carcinoma (Colo205, #CCL-222 and HT29, #HTB-38), prostate carcinoma (LNCaP, #CRL-1740) and breast carcinoma (ZR-75-1, #CRL-1500) were purchased and stored in liquid nitrogen. Cells were cultured in Roswell Park Memorial Institute media (RPMI-1640) or minimum essential medium with Earl's salts (EMEM) supplemented with 10% Foetal calf serum (FCS, Sigma) and cultured using a 37° C. cell culture incubator (Forma Scientific, NinoLab, Kungsbacka, Sweden) with 5% $CO_2$ humidified atmosphere. Tumor cell lines were handled aseptically using a laminar airflow (LAF) bench (Holten 2448, Ninolab, Sweden) and stored in a liquid nitrogen tank and were initiated in culture as previously described (Falk P. Experimental models of the peritoneal environment: Effects of TGF-beta and Hyaluronan. Göteborg: University of Gothenburg; 2008). Briefly, ampoules of frozen cells were thawed by submerging into a 37° C. water bath for 45 s. Cells were resuspended in 10 ml of preheated RPMI-1640 with 10% FCS and centrifuged in 260 g for 10 min. With supernatant discarded, cell pellets were further resuspended with 5 ml complete medium into 25 $cm^2$ cell culture flasks (Cell+, Sarstedt, Nümbrecht, Germany). Tumor cells were cultured until sub-confluence and further sub-cultured with Trypsin (0.5%), EDTA (0.2%) solution (T4174, TE-10x, Sigma) in sterile sodium chloride. Culture media was changed two-three times a week. Culture flasks (Cell+, Sarstedt, Nümbrecht, Germany) and culture plates (Falcon/BD, Franklin Lakes, N.J., USA) were used for experimental set-ups. Cells were regularly monitored using an inverted microscope connected to a digital photo equipment (Axiovert 25 and Axiovision, Zeiss, Carl Zeiss AG, Germany) (FIG. 1). Described culture techniques and equipment have been used extensively in the laboratory Substances Ivermectin (Sigma) is hydrophobic and was diluted in 95% alcohol in the first step and then subsequently gently diluted to 1×10e-4 mol/L by adding additional solvent with decreasing amount of alcohol. The following concentrations were used in the experimental set-up; 1×10e-4 to 1×10e-10 mol/L.

Abamectin (Sigma) is hydrophobic and was diluted using methanol and subsequentially gently diluted with decreasing amount of alcohol. Concentrations of 10 and 100 μmol/L were used.

Selamectin (Sigma) is hydrophobic and according to manufacturing instruction dimethylsulphoxide (DMSO) was used as solvent. Further dilutions were made using gently dilution with decreasing amounts of alcohol. Concentrations of 10 and 100 μmol/L were used.

Since the alcohol concentrations reach above 1% in assay concentration for the highest avermectin concentrations control experiments were performed using the same alcohol concentration but without active substance.

Ketoconazole is an antifungal drug used in fungal skin infections and in combination with chemotherapy. Ketoconazole is a hydrophobic substance and was dissolved in methanol and further gently diluted using culture media. Concentrations of 10, 20 and 40 μmol/L were used alone and together with ivermectin, selamectin or abamectin.

Albendazole is a drug indicated for the treatment of a variety of worm infestations. Albendazole is a hydrophobic substance and was dissolved in DMSO and further gently diluted using alcohol and culture media. Concentrations of 20 and 40 μmol/L were used alone and together with ivermectin, selamectin or abamectin.

Ibuprofen (Sigma) is a nonsteroidal anti-inflammatory drug (NSAID) used for relief symptoms from pain and fever. Ibuprofen is hydrophilic and was initially diluted using sterile water and further diluted using culture medium RPMI-1640 or EMEM. Concentrations of 10, 20 and 40 μmol/L were used alone or together with ivermectin, selamectin or abamectin.

Diclofenac sodium (Sigma) is a nonsteroidal anti-inflammatory drug (NSAID) used for relief symptoms from pain. Diclofenac sodium is hydrophilic and was initially diluted using sterile water and further diluted using culture medium RPMI-1640 or EMEM. Concentrations of 10, 40 and 100 μmol/L were used alone or together with ivermectin, selamectin or abamectin.

Celecoxib (Sigma) is a NSAID substance and a specific COX-2 inhibitor. Celecoxib is strongly hydrophobic substance and it was initially dissolved in dimethylsulfoxide (DMSO) to 32 mmol/L. Further dilutions were made due to gently addition of a 50/50 (Alcohol 70%/RPMI 1640) mixture to 3.2 mmol/L. Additional gentle addition of RPMI 1640+1% fetal calf serum (FCS) were made to 1 mmol/L. Additional serial dilutions using RPMI 1640+1% FCS to 10, 20 and 40 μmol/L were used alone or together with ivermectin, selamectin or abamectin.

Morphology and Viability

The effect of Ivermectin, selamectin, abamectin alone, or in combination with ketoconazole, albendazole, ibuprofen, diclofenac and celecoxib on the morphology of cultured human tumor cells was studied. The effect of ivermectin in the presence of increasing concentration of ivermectin was also investigated. Cells were grown into sub-confluence and then sub-cultured into 12 and 24 well plates (Sarstedt, Falcon/BD) for morphology studies, or in 96 well plates (Sarstedt, Falcon/BD) for proliferation studies. Viability of urinary bladder cells was studied using the tryphan blue exclusion method (Freshney R. Culture of animal cells: A manual of basic techniques. New York: Alan R Liss Inc; 1987).

Proliferation

The proliferation rates of the different human tumor cell lines were studied using a method based on the conversion of a sodium salt (XTT-assay, Sigma) into a stable orange color that could be analyzed in a spectrophotometer. The color change is proportional to the mitochondrial dehydrogenase activity resulting in an effective technique for measuring cell toxicity (Roehm N W, Rodgers G H, Hatfield S M, Glasebrook A L. An improved colorimetric assay for cell proliferation and viability utilizing the tetrazolium salt XTT. J Immunol Methods 1991;142(2):257-65) or cell proliferation. The color change was measured using a 96-well plate reader with software to calculate the absorbance at 450 nm (V-max/Softmax Pro, Molecular Devices, USA). Cells were cultured until approx 50% confluence and then pre-incubated for 24 h with RPMI-1640 or EMEM containing 1% FCS only. RPMI 1640 and EMEM without phenol red was used during the experiments to reduce the red color background signal in the XTT-assay.

Prior to the experimental start all cells were gently washed once with RPMI 1640 and EMEM with 1% FCS.

Increasing concentrations of substance ivermectin was added with an 8-channel pipette (Titertek, Kem-En-Tec, Taastrup, Denmark) together with sterile pipette tips (Molecular Bioproducts, San Diego, Calif., USA). Cell cultures including active substances were incubated for 24 hours (and 96 hours). Untreated wells including culture medium only served as untreated controls. The XTT-assay substrate was added and after gentle agitation using a micro plate shaker, absorbencies at 450 and 650 nm were measured. Levels from medium were subtracted and compared with control wells, using culture medium only.

Statistics

The non-parametric Kruskal-Wallis test was used to detect overall differences and if significant, a Mann-Whitney U test was performed between individual groups. A p-value<0.05 were considered statistically significant. Results are presented in the figures as Mean±SEM. Results in tables are presented as Mean±SD. All statistical calculations were performed using the StatView 5.0 package (Abacus Concepts, Berkeley, Calif., USA). Calculations of absorbance and concentrations were analyzed with the Softmax Pro software using both linear and 4-parameter curve fit (Softmax Pro, Molecular Devices, USA).

Results

Cell Culture

Cultures were established from all tested tumor cell lines. Tumor cells could be cultured, sub-cultured, frozen and refrozen into liquid nitrogen without affecting growth performance.

Ivermectin Affects Morphology and Viability of Cultured Tumor Cell Lines

Figure 2:
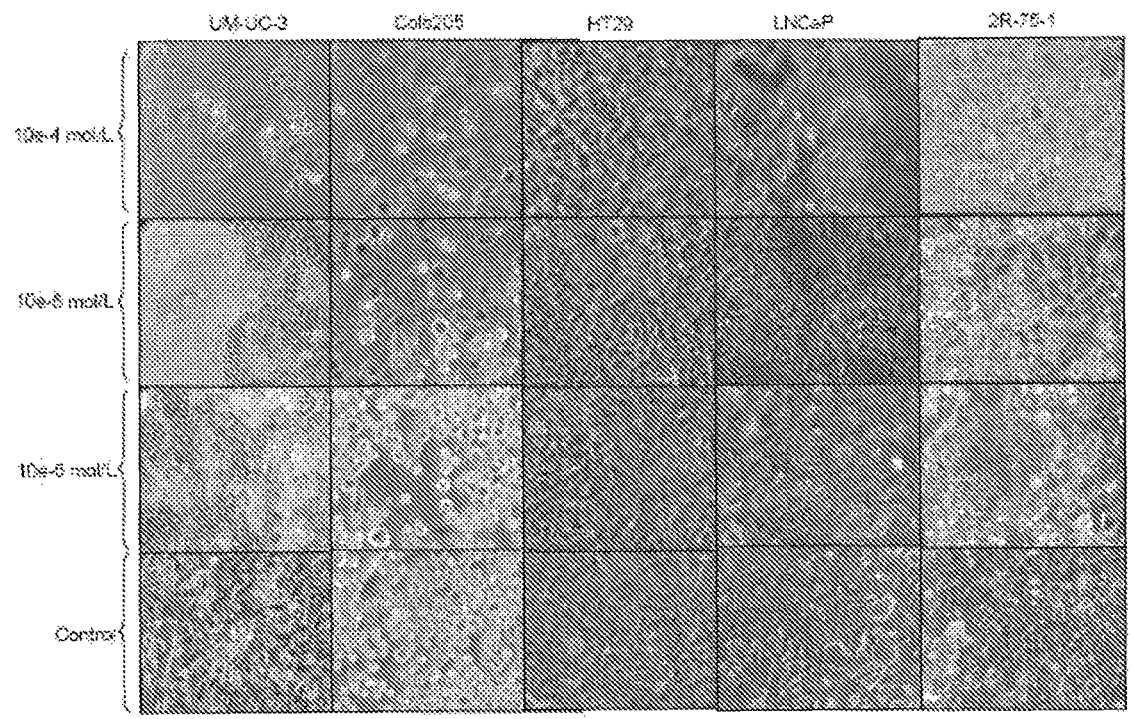
FIG. 2 shows morphological effects of Ivermectin on cultured tumor cell lines.

The presence of ivermectin affected all the human cultured tumor cell lines in a negative manner compared to cells treated with the medium control. Most negative observations were made in the concentration interval 10e-4 to 10e-6 mol/L. Most of the tumor cells were affected with damaged cell structure and/or cell loss in anchorage dependent tumor cells. FIG. 2 shows morphological effects of ivermectin on cultured tumor cell lines. It can be seen that concentrations above 10e-5 mol/L affected morphology and proliferation on most of the cultured tumor cells. The colorectal cell lines HT29 was not morphologically affected even at the highest concentration, while the Colo205 line was affected even at 10e-6 mol/L. Both the prostate cell line LNCaP and the breast cancer cell line 2R-75-1 was affected by the highest concentration 10e-4 mol/L only (Objective magnification× 20).

Figure 3:
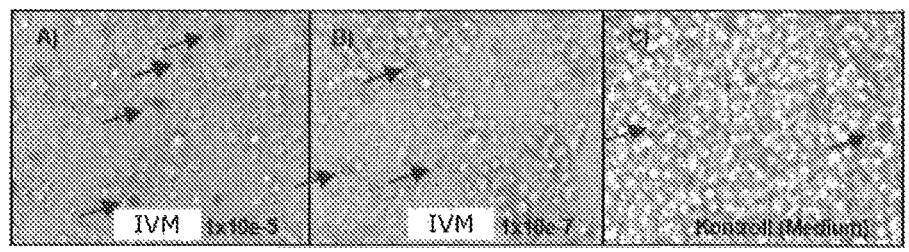
FIG. 3 shows Tryphan blue exclusion of human urinary bladder cancer cells.

FIG. 3 shows Tryphan blue exclusion of human urinary bladder cancer cells. It can be seen that ivermectin affected cells in a dose-dependent manner (3a-b), compared to untreated medium control (3c).

Figure 4:
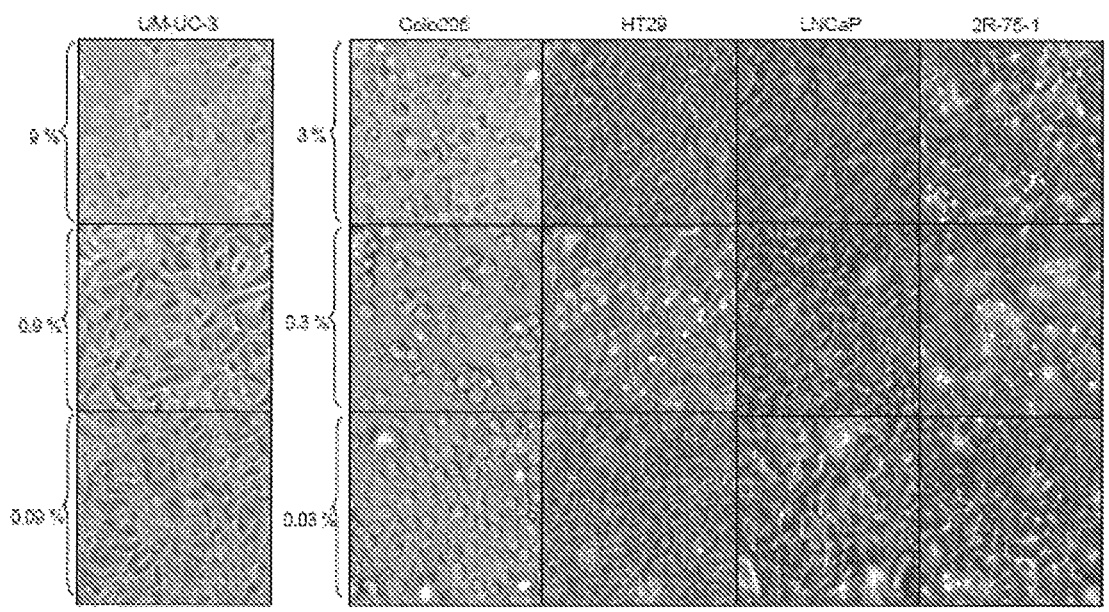
FIG. 4 shows effects of different alcohol concentrations on human tumor cell lines.

It is notable that an alcohol concentration above 3% also affected most of the tumor cells in a negative manner. In the initial experiments with the urinary bladder cells the alcohol concentration in the highest ivermectin concentration were 9% however, during the later experiments this concentration was reduced to 3%. This was achieved due to gentle dilution adding small amounts of dilution medium, instead of strictly performed serial dilutions. Morphological effects on the cultured tumor cells are illustrated in FIG. 4.

Ivermectin Affects Proliferation Rate of Cultured Tumor Cell Lines

The presence of ivermectin decreased the proliferation rate of all human tumor cells compared to cells treated with medium only (see Table 2). Proliferation rates are expressed as mean±standard deviation for each concentration in per cent compared to untreated medium control. At ivermectin 10e-4 mol/L all cell lines reduced their proliferation rate.

For the urinary bladder cell line (UM-UC-3) the addition of ivermectin reduced proliferation significantly ($p<0.01$) compared to untreated control, with most pronounced effect at 10e-4 mol/L (34±3%, $p<0.05$) and 10e-5 (34±8%, $p<0.05$).

Figure 5:
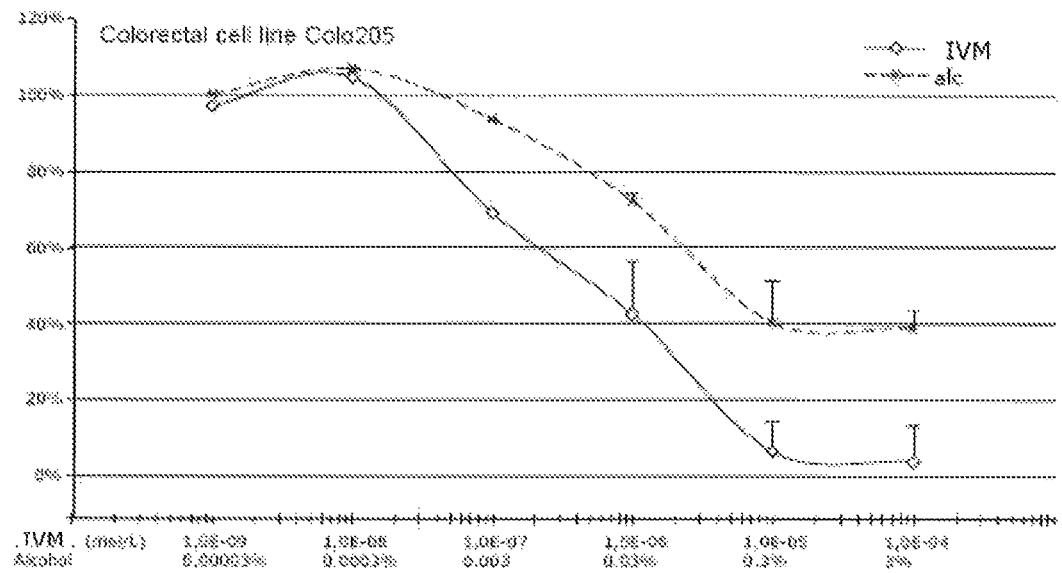
FIG. 5 shows proliferation rates in % of untreated control for the colorectal tumor cell line Colo205.

In the colorectal cell line (Colo205) ivermectin reduced the overall proliferation rate ($p<0.0001$) compared to control. FIG. 5 shows the proliferation rates in % of untreated control for the colorectal tumor cell line Colo205. This effect was most distinct at 10e-4 mol/L (4±1%, $p<0.01$), at 10e-5 mol/L (6±1%, $p<0.01$), at 10e-6 mol/L (42±12%, $p<0.01$) and at ivermectin 10e-7 mol/L (69±9%, $p<0.05$). Notable is that the dilution buffer including the same alcohol concentration, but without active substance ivermectin, also affected proliferation (Proliferation in %, Mean±SD compared to control).

In the other colorectal cell line (HT29) the overall proliferation rate was significantly reduced by the addition of ivermectin ($p<0.0001$) with most effect seen at 10e-4 (5±1%, $p<0.01$) and 10e-5 (85±11%, $p<0.05$) mol/L.

The prostatic cell line (LNCaP) significantly reduced the proliferation rate ($p<0.0001$) compared to untreated control when treated with ivermectin. This effect was most pronounced at 10e-4 (8±1%, $p<0.01$) and 10e-5 (753%, $p<0.01$) mol/L.

Finally, also the human breast cancer cell line (2R-75-1) was affected by ivermectin by reduction in cell proliferation rate ($p<0.01$) compared to untreated control. This effect was only seen at 10e-4 mol/L (7±2%, $p<0.01$). Experimental set ups with the different human cell lines were run in duplicates with 6-8 replications in each experiment. Results are summarized in Table 2.

TABLE 2

| Cell lines | 10e-9 | 10e-8 | 10e-7 | 10e-6 | 10e-5 | 10e-4 |
|---|---|---|---|---|---|---|
| UM-UC-3 | 100 ± 3% | 96 ± 5% | 95 ± 9% | 91 ± 3% | 34 ± 6% | 34 ± 3% |
| Urinary bladder | (n.s.) | (n.s.) | (n.s.) | (n.s.) | ($p < 0.05$) | ($p < 0.05$) |
| Colo205 | 97 ± 14% | 104 ± 8% | 69 ± 9% | 42 ± 12% | 6 ± 1% | 4 ± 1% |
| Colorectal Ca | (n.s.) | (n.s.) | ($p < 0.05$) | ($p < 0.01$) | ($p < 0.01$) | ($p < 0.01$) |
| HT29 | 109 ± 14% | 112 ± 12% | 106 ± 9% | 91 ± 5% | 85 ± 11% | 5 ± 1% |
| Colorectal Ca | (n.s.) | (n.s.) | (n.s.) | (n.s.) | ($p < 0.05$) | ($p < 0.01$) |
| LNCaP | 91 ± 4% | 93 ± 5% | 94 ± 5% | 99 ± 4% | 75 ± 3% | 8 ± 1% |
| Prostate Ca | (n.s.) | (n.s.) | (n.s.) | (n.s.) | ($p < 0.01$) | ($p < 0.01$) |
| 2R-75-1 | 114 ± 31% | 128 ± 30% | 105 ± 35% | 95 ± 37% | 124 ± 34% | 7 ± 2% |
| Breast Ca | (n.s.) | (n.s.) | (n.s.) | (n.s.) | (n.s.) | ($p < 0.01$) |

As earlier described there are a certain effects of alcohol present in the dilution media. This was most pronounced when the colorectal cell line Colo205 was investigated.

Even alcohol concentration below 3% affected these cell types in a negative manner (FIGS. 4 and 5).

Figure 6:
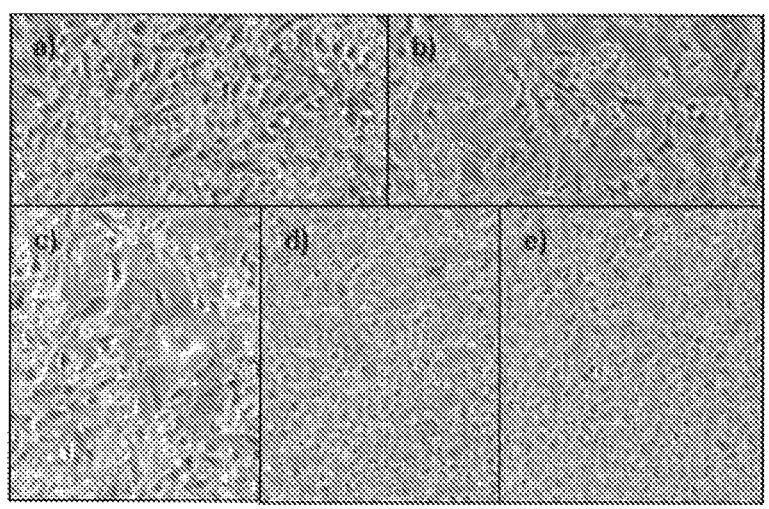
FIG. 6 shows the morphology of urinary bladder cells (UM-UC-3) after 24 hours with ivermectin stimulation with or without the combination of ketoconazole.
Figure 9:
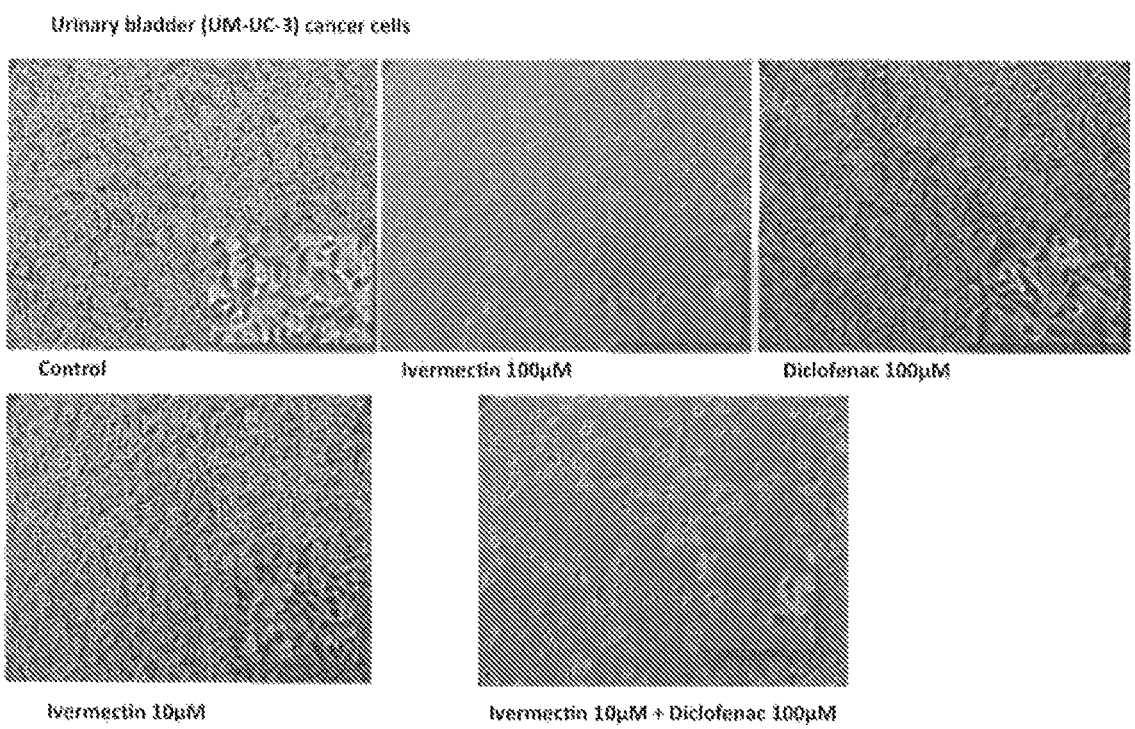
FIG. 9 shows the morphology and synergistic effects of ivermectin and diclofenac in human urinary tumor cell line (UM-UC-3).

Ivermectin in Combination with Ketoconazole, Ibuprofen, Diclofenac and/or Celecoxib Affect Morphology and Viability of Cultured Tumor Cell Lines In the urinary bladder cell line (UM-UC-3) a synergistic effect were seen when ivermectin were combined with ketoconazole, diclofenac or ibuprofen. Cells were damaged and detached from the culture upon stimulation. Cell structure was damaged and a lot of cells stimulated by the combination showed a ballooned appearance, compared to untreated medium control. FIG. 6 shows the morphology of urinary bladder cells (UM-UC-3) after 24 hours with ivermectin stimulation. The morphology of the cells was affected when treated with ivermectin (100 μM). However, a synergistic effect was seen with affected morphology when ivermectin were combined with ketoconazole (10, 20 and 40 μM). A) control cells, B) Cells affected of ivermectin, 100 μM. C-E) Synergistic effects were seen with ivermectin 100 μM in combination with ketoconazole 10 μM c), 20 μM, d) and 40 μM (e) compared to ivermectin 100 μM alone (b). Additional, effects were also seen when ivermectin and diclofenac were combined. FIG. 9 indicates synergistic effect on the morphology when ivermectin 10 μM and diclofenac 100 μM were combined.

Figure 7:
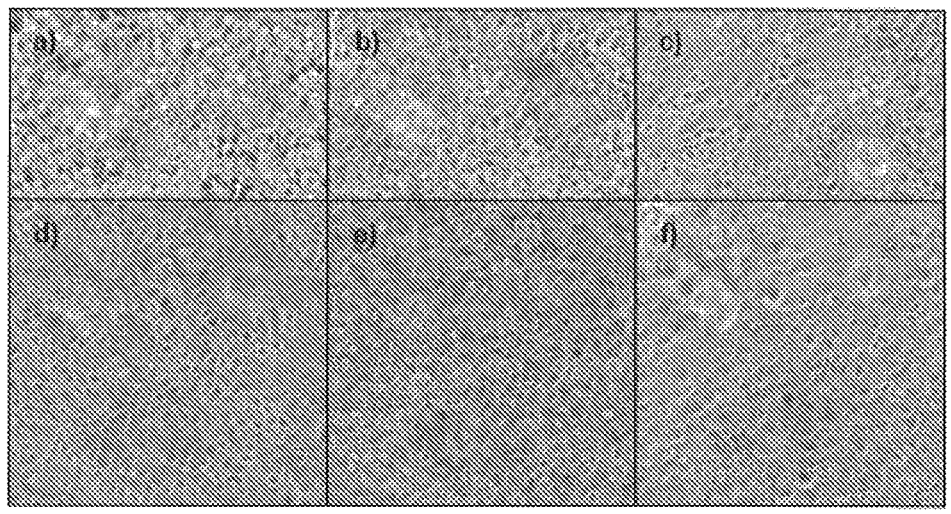
FIG. 7 shows the morphology of colorectal cells (Colo205) 24 hours after ivermectin stimulation.

In the colorectal tumor cell line (Colo205) affected cell structure was seen with ivermectin 1001 μM, but no effect were seen at ivermectin 10 μM. A small synergistic effect was seen when ivermectin 100 μM were combined with ketoconazole 10, 20 and 40 μM, similar to the UM-UC-3 cells. Surprisingly, a synergistic effect was also seen at ivermectin 10 μM in combination with ketoconazole 10, 20 and 40 μM. In these cultures cells showed an increase in cell detachment and ballooned structure, compared to untreated medium control (FIG. 7). Similar to the urinary bladder cell line the combination of ivermectin 10 μM and diclofenac 1001 μM generated a synergistic increase in cell death for these cells.

The colorectal cell line HT29 was affected when ivermectin 100 μM was used. No synergistic effects were seen in ivermectin 10 or 100 μM, when combined with ketoconazole, ibuprofen and celecoxib, compared to untreated control. A possible synergistic effect was seen when ivermectin 10 μM were combined with diclofenac 40 and 100 μM. Moreover, an effect was seen in the morphological appearance when ivermectin were combined with albendazole 20 and 40 μM.

Figure 8:
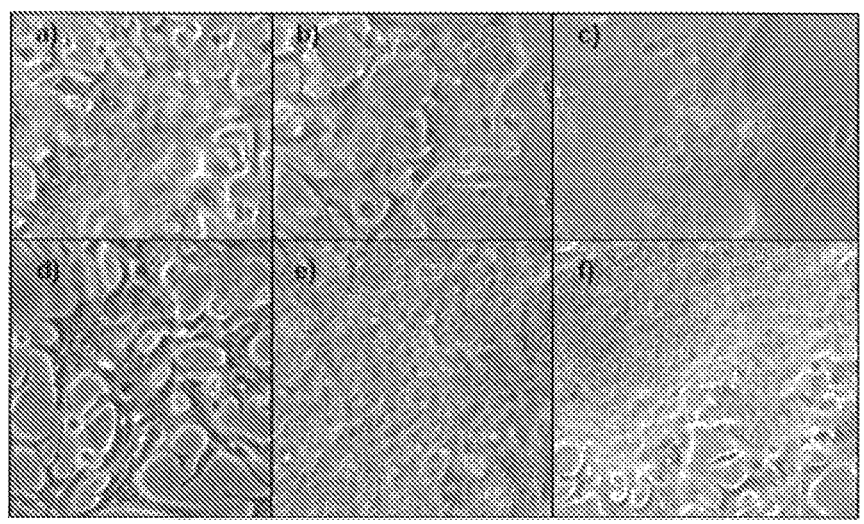
FIG. 8 shows the morphology of prostate cells (LNCaP) 24 hours after ivermectin stimulation.

FIG. 8 shows that the prostatic cell line LNCaP was affected after high doses of ivermectin (100 μM), with cell damage and detachment of cells 24 hours after ivermectin stimulation (c). No effect was seen at ivermectin 1 (a) and 10 μM (b). Ketoconazole did affect morphology at concentrations 20 and 40 μM with cell death and detachment as expected. At ketoconazole 10 μM (d) cells were not microscopically affected, but interestingly the combination with ivermectin 10 μM affected the morphology and caused partly detachment of cells from the surface (e), f) Control. A small synergistic effect was seen when ivermectin 10 μM were combined with diclofenac 40 μM and 100 μM.

Ivermectin in Combination with Ketoconazole, Ibuprofen and Celecoxib Affects the Proliferation Rate In the urinary bladder cell line UM-UC-3 (Table 3) a synergistic effect in proliferation rate were seen when ivermectin was combined with ketoconazole, ibuprofen or celecoxib. Ivermectin only reduced the proliferation rate to 90±1% ($p<0.05$, n=6). Interestingly, when ivermectin (100 μM) were used together with ketoconazole (20 μM) the proliferation rate decreased to 63±18% ($p<0.05$, n=6) and in combination with ketoconazole (40 μM) it decreased to 42±24% ($p<0.01$, n=6) compared to untreated medium control (Table 3).

TABLE 3

| Urinary bladder UM-UC-3 | Control | IVM 1 μmol/L | IVM 10 μmol/L | IVM 100 μmol/L |
|---|---|---|---|---|
| Control | 100 ± 1% | 99 ± 1% | 105 ± 3% | 90 ± 1% ($p < 0.05$) |
| Keto 10 μmol/L | 95 ± 6% | 105 ± 4% | 113 ± 4% | 84 ± 23% |
| Keto 20 μmol/L | 99 ± 6% | 101 ± 5% | 111 ± 3% | 63 ± 18% ($p < 0.05$) |
| Keto 40 μmol/L | 103 ± 2% | 101 ± 6% | 110 ± 4% | 42 ± 24% ($p < 0.01$) |
| Ibup 10 μmol/L | 103 ± 2% | 107 ± 5% | 110 ± 3% | 102 ± 11% |
| Ibup 20 μmol/L | 106 ± 2% | 110 ± 4% | 109 ± 7% | 86 ± 18% |
| Ibup 40 μmol/L | 99 ± 3% | 112 ± 4% | 114 ± 4% | 34 ± 21% ($p < 0.01$) |
| Cele 10 μmol/L | 103 ± 9% | 111 ± 4% | 112 ± 6% | 96 ± 22% |
| Cele 20 μmol/L | 100 ± 6% | 111 ± 3% | 110 ± 5% | 85 ± 16% |
| Cele 40 μmol/L | 106 ± 1% | 113 ± 3% | 111 ± 1% | 97 ± 4% |

In the colorectal cell line (Colo2065) ivermectin alone affected proliferation rate at the 100 μM level. Synergistic effects in proliferation rate were seen when ivermectin were combined with ketoconazole or ibuprofen. This effect was not only seen at ivermectin 100 μM, but also at 10 μM. When ivermectin 10 μM were combined with ketoconazole 10, 20 or 40 μM the proliferation rate decreased to 83.1±16.9% ($p<0.05$, n=6) with ketoconazole 10 μM, 88.1±17.6% ($p<0.05$, n=6) using ketoconazole 20 μM and at ketoconazole 40 μM the proliferation rate decreased to 57.9±24.6% ($p<0.01$, n=6), compared to medium control (see Table 4).

The colorectal cell line HT29 was affected in decreased proliferation rate when ivermectin 100 μM was used. No additional effects in proliferation rate were seen combined with ketoconazole, ibuprofen or celecoxib, compared to untreated control. However, when ivermectin 10 μM was combined with albendazole 20 and 40 μM affected morphology were seen with decreased tumor growth.

TABLE 4

| Colorectal Colo205 | Control | IVM 1 μmol/L | IVM 10 μmol/L | IVM 100 μmol/L |
|---|---|---|---|---|
| Control | 100.2 ± 5.5% | 101.3 ± 4.9% | 97.7 ± 8.5% | 69.4 ± 11.5% ($p < 0.05$) |
| Keto 10 μmol/L | 94.8 ± 6.3% | 89.4 ± 17.9% | 83.1 ± 16.9% ($p < 0.05$) | 67.0 ± 5.0% ($p < 0.01$) |
| Keto 20 μmol/L | 93.4 ± 8.1% | 93.7 ± 11.0% | 88.1 ± 17.6% ($p < 0.05$) | 53.5 ± 7.3% ($p < 0.01$) |

TABLE 4-continued

| Colorectal Colo205 | Control | IVM 1 µmol/L | IVM 10 µmol/L | IVM 100 µmol/L |
|---|---|---|---|---|
| Keto 40 µmol/L | 72.1 ± 15.5% | 76.3 ± 7.1% | 57.9 ± 24.6% (p < 0.01) | 30.1 ± 6.8% (p < 0.01) |
| Ibup 10 µmol/L | 90.1 ± 8.8% | 88.4 ± 19.2% | 105.8 ± 14.5% | 79.1 ± 20.1% |
| Ibup 20 µmol/L | 92.2 ± 8.2% | 93.2 ± 9.9% | 97.3 ± 20.6% | 59.9 ± 5.3% (p < 0.05) |
| Ibup 40 µmol/L | 90.8 ± 6.3% | 100.4 ± 8.3% | 95.3 ± 7.1% | 59.6 ± 21.2% (p < 0.05) |
| Cele 10 µmol/L | 98.7 ± 15.8% | 96.7 ± 15.7% | 92.3 ± 12.4% | 63.5 ± 12.4% |
| Cele 20 µmol/L | 94.8 ± 2.5% | 94.8 ± 2.6% | 100.4 ± 9.4% | 68.0 ± 13.9% |
| Cele 40 µmol/L | 94.5 ± 6.6% | 94.5 ± 6.6% | 93.4 ± 51% | 66.7 ± 6.3% |

The prostatic cell line (LNCaP) reduced the proliferation rate compared to untreated control when ivermectin at 100 µM was used alone or in combination with ketoconazole, ibuprofen or celecoxib as can be seen in Table 5.

TABLE 5

| Prostata Ca LNCaP | Control | IVM 1 µmol/L | IVM 10 µmol/L | IVM 100 µmol/L |
|---|---|---|---|---|
| Control | 100.5 ± 0.5% | 95.4 ± 0.6% | 106.4 ± 2.2% | 45.7 ± 2.2% (p < 0.05) |
| Ket 10 µmol/L | 104.6 ± 3.0% | 118.3 ± 0.2% | 86.0 ± 0.2% (p < 0.05) | 48.1 ± 2.5% (p < 0.05) |
| Ket 20 µmol/L | 76.3 ± 2.3% (p < 0.05) | 78.3 ± 1.4% (p < 0.05) | 65.7 ± 1% (p < 0.05) | 43.4 ± 0.8% (p < 0.05) |
| Ket 40 µmol/L | 68.0 ± 1.8% (p < 0.05) | 71.3 ± 2.4% (p < 0.05) | 63.8 ± 2.3% (p < 0.05) | 39.7 ± 3.6% (p < 0.05) |

Ketoconazole alone at 20 and 40 µM decreased the proliferation rate, compared to untreated medium controls. A synergistic effect in proliferation rate was seen when ivermectin 10 µM and ketoconazole 10 µM were combined 86.0±0.2% (p<0.05, n=6). This effect was not seen with ivermectin 10 µM (106.4±2.2) and ketoconazole 10 µM (104.6±3.0) alone, compared to untreated control.

The breast cell line (ZR-75-1) reduced the proliferation rate compared to untreated control when ivermectin 100 µM was used alone or in combination with ketoconazole, ibuprofen or celecoxib. Since ivermectin alone reduced proliferation rate at both 10 and 100 µM no additative effects could be seen when combinations were made. However, surprisingly to the authors, synergistic effects were seen already at ivermectin 1 µM when combined with ibuprofen 20 and 40 µM and celecoxib 40 µM (see Table 6).

TABLE 6

| Breast Ca ZR-75-1 | Control | IVM 1 µmol/L | IVM 10 µmol/L | IVM 100 µmol/L |
|---|---|---|---|---|
| Control | 99.9 ± 4.6% | 90.0 ± 5.2% | 60.5 ± 10.6% (p < 0.01) | 14.4 ± 1.7% (p < 0.01) |
| Ibupr 10 µmol/L | 115.2 ± 3.8% | 86.1 ± 11.5% ns | 87.3 ± 1.4% (p < 0.01) | 14.4 ± 1.9% (p < 0.01) |
| Ibupr 20 µmol/L | 116.2 ± 1.9% | 80.7 ± 8.4% (p < 0.01) | 82.9 ± 4.0% (p < 0.01) | 13.5 ± 1.7% (p < 0.01) |
| Ibupr 40 µmol/L | 108.7 ± 6.7% | 58.7 ± 1.5% (p < 0.01) | 56.2 ± 30.2% (p < 0.01) | 13.6 ± 2.1% (p < 0.01) |
| Cele 10 µmol/L | 116.5 ± 4.4% | 101.1 ± 3.8% | 69.6 ± 6.2% (p < 0.01) | 12.3 ± 2.0% (p < 0.01) |
| Cele 20 µmol/L | 110.6 ± 13.3% | 99.5 ± 9.4% | 68.6 ± 10.9% (p < 0.01) | 12.2 ± 2.1% (p < 0.01) |
| Cele 40 µmol/L | 95.2 ± 4.9% | 77.0 ± 17.6% (p < 0.01) | 71.9 ± 5.8% (p < 0.01) | 5.1 ± 2.6% (p < 0.01) |

As earlier described there are a certain effects of alcohol present in the dilution media. Alcohol concentration above 3% affected cell proliferation in a negative manner. This was most pronounced when the colorectal cell line Colo205 was investigated; even alcohol concentration below 3% affected these cell types in a negative manner.

Figure 10:
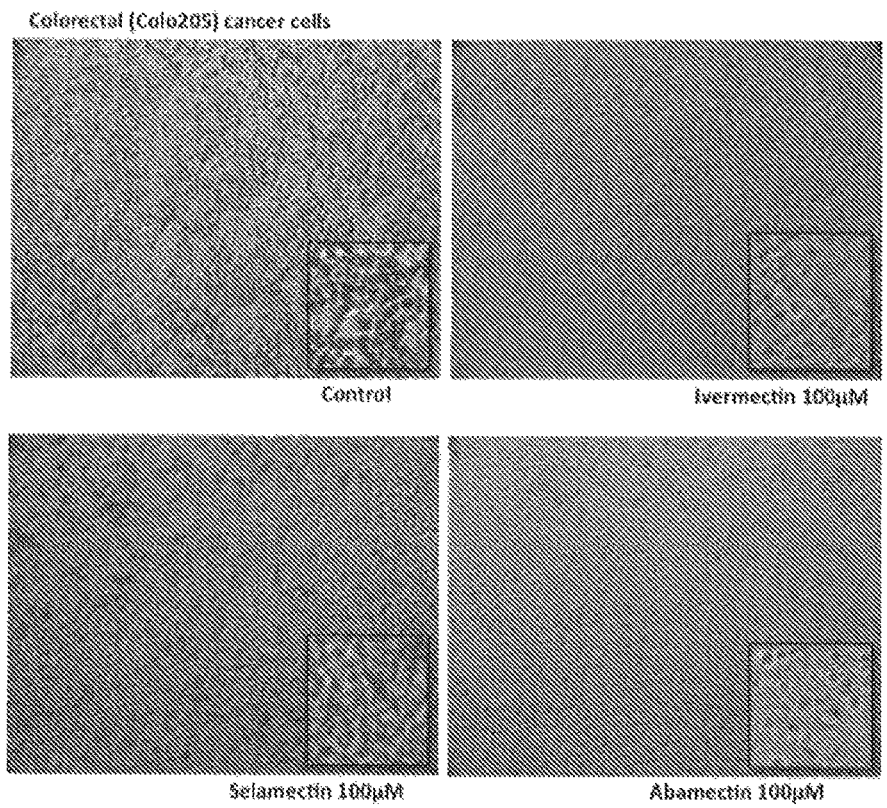
FIG. 10 shows the morphology and comparable effects of ivermectin, selamectin and abamectin on a colorectal (Colo205) cell line.

In order to evaluate more members from the avermectin family selamectin and abamectin were investigated using similar concentrations as for ivermectin. Morphology studies indicated that both selamectin and abamectin at 100 µM have similar negative effect on morphology as for ivermectin 100 µM. This is demonstrated for the colorectal cell line (Colo205) as indicated in FIG. 10.

Figure 11:
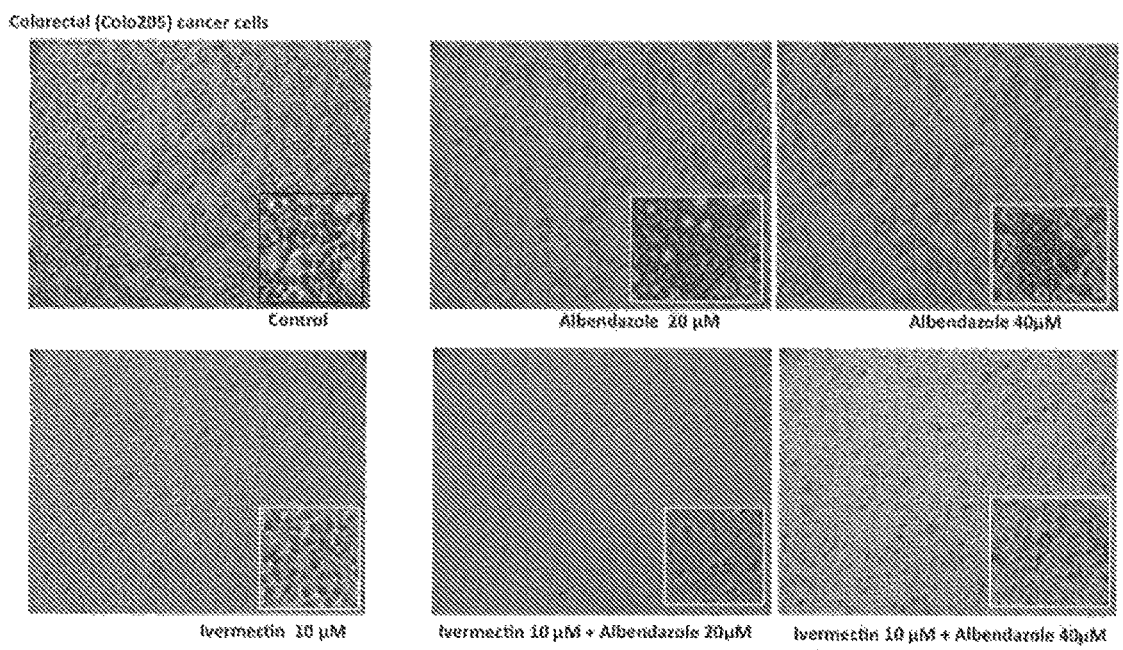
FIG. 11 shows the morphology and synergistic effects of ivermectin and albendazole on a colorectal (Colo205) cell line.

Moreover, when albendazole were added at 20 and 40 µM together with ivermectin 10 µM a synergistic effect was seen in the same cell line with decreased growth of cells. This was not seen when ivermectin 10 µM and albendazole 20 and 40 µM were tested alone (FIG. 11).

DISCUSSION

The present studies are based on a case report describing a middle age man suffering from an advanced urothelial cancer with extensive metastasis. Due to a tropical infection this patient received the substance ivermectin. Surprisingly to the authors, this treated both the tropical infection and the urothelial cancer. The reason for this is not known however a direct effect of the substance ivermectin could not be precluded. The patient case in the present study did not receive any other medication than substance ivermectin.

When verifying the effect of ivermectin on a palette of human tumor cells, it could be demonstrated that ivermectin, in a dose-response manner, reduces the proliferation rate in human cultured tumor cells. Cells used derived from urinary bladder, colorectal region, prostate and mammary glands. Ivermectin reduced the cell proliferation rate in micromolar concentrations in the five different human tumor cell lines, from four different locations. All cell lines reduce the proliferation rate at 100 micromolar and several of them at even lower concentrations.

Additionally, when selamectin and abamectin, other members in the avermectin family, was used alone or in combination with members from the NSAID family similar effects were seen on several of the different tumor cell lines tested in the experimental models. Thus, the observed effect alone or in combination with other substances was not only from the substance ivermectin, but seems also be generated from several members of the avermectin family.

However, the above experiments demonstrated that ivermectin and other members from the avermectin family (i.e in particular abamectin and selamectin), in combination with ketoconazole, albendazole, ibuprofen, diclofenac and/or celecoxib in a dose-response manner exhibited a synergistic effect on cell morphology and/or reduction in proliferation rate in human cultured tumor cell lines. Cells used derived from urinary bladder, colorectal region, breast and prostate tissue.

In conclusion, the avermectin compounds ivermectin, abamectin andselamectin reduced cell proliferation in urinary, colorectal, prostate and breast tumor cell lines. When combined with ketoconazole, ibuprofen, diclofenac or celecoxib, the combination provided synergistic effects in affecting the morphology of cultured tumor cells and in the reduction of the proliferation rate. This might introduce several lines of therapeutic substance for all those individuals that suffer from several forms of cancer.

The invention claimed is:

1. A composition comprising an effective amount of ivermectin in combination with an effective amount of a non-steroidal anti-inflammatory drug (NSAID) or suitable pharmaceutically acceptable salts thereof, for use in the inhibition of tumor growth and treatment of cancer, wherein the non-steroidal anti-inflammatory drug (NSAID) is selected from the group consisting of a salicylate compound, a propionie acid compound, a selective COX-2 inhibitor, and an acetic acid compound.

2. The composition according to claim 1, wherein the cancer is selected from the group consisting of urothelial cancer, colorectal cancer, prostate cancer, breast cancer, and any combination thereof.

3. The composition according to claim 1, wherein the cancer is urothelial entice.

4. The composition according to claim 1, wherein the cancer is colorectal cancer.

5. The composition according to claim 1, wherein the cancer is breast cancer.

6. The composition according to claim 1, wherein the cancer is prostate cancer.

7. The composition according to claim 1, wherein the propionic acid compound is selected from the group consisting of ibuprofen, naproxen, fenoprofen, ketoprofen, flurbiprofen, oxaprozin, and loxoprofen.

8. The composition according to claim 7, wherein the propionic acid compound is ibuprofen.

9. The composition according to claim 8, wherein the cancer is selected from the group consisting of urothelial cancer, colorectal cancer, prostate cancer, breast cancer, and any combination thereof.

10. The composition according to claim 1, wherein the acetic acid compound is selected from the group consisting of indomethacin, sulindac, etodolac, ketorolac, diclofenac, and nabumetone.

11. The composition according to claim 1, wherein, the acetic acid compound is diclofenac.

12. The composition according to claim 11, wherein the cancer is selected from the group consisting of urothelial cancer, colorectal cancer, prostate cancer, breast cancer, and any combination thereof.

13. The composition according to claim 1, wherein the salicylate compound is selected from the group consisting of acetylsalicylic acid, diflunisal, and salsalate.

14. The composition according to claim 1, wherein the salicylate compound is acetylsalicylic acid.

15. The composition according to claim 14, wherein the cancer is selected from the group consisting of urothelial cancer, colorectal cancer, prostate cancer, breast cancer, and any combination thereof.

16. The composition according to claim 1, wherein the selective COX-2 inhibitor is celecoxib.

17. The composition according to claim 16, wherein the cancer is selected from the group consisting of urothelial cancer, colorectal cancer, prostate cancer, breast cancer, and any combination thereof.

18. A composition comprising an effective amount of ivermectin in combination with an effective amount of a non-steroidal anti-inflammatory drug (NSAID) or suitable pharmaceutically acceptable salts thereof, for use in the inhibition of tumor growth and treatment of cancer, wherein the NSAID is selected from the group consisting of ibuprofen, diclofenac acetylsalicylic and celecoxib.

19. The composition according to claim 18, wherein the cancer is selected from the group consisting of urothelial cancer, colorectal cancer, prostate cancer, breast cancer and any combination thereof.

20. The composition according to claim 18, wherein the cancer is urothelial cancer.

21. The composition according to claim 18, wherein the cancer is colorectal cancer.

22. The composition according to claim 18, wherein the cancer is breast cancer.

23. The composition according to claim 18, wherein, the cancer is prostate cancer.

* * * * *

UNITED STATES PATENT AND TRADEMARK OFFICE
CERTIFICATE OF CORRECTION

PATENT NO. : 9,782,424 B2
APPLICATION NO. : 14/366604
DATED : October 10, 2017
INVENTOR(S) : Edlund et al.

It is certified that error appears in the above-identified patent and that said Letters Patent is hereby corrected as shown below:

In the Specification

Column 6, Line 25: Please correct "lomoxicam" to" read -- lornoxicam --

Column 20, Line 42: Please correct "753%" to read -- 75 ± 3% --

Column 21, Line 28: Please correct "1001 μM" to read -- 100 μM --

Column 21, Line 39: Please correct "1001 μM" to read -- 100 μM --

In the Claims

Column 25, Claim 1, Line 66: Please correct "propionie" to read -- propionic --

Signed and Sealed this
Tenth Day of July, 2018

Andrei Iancu
*Director of the United States Patent and Trademark Office*